United States Patent
Yamaguchi

(10) Patent No.: US 8,343,759 B2
(45) Date of Patent: Jan. 1, 2013

(54) MAMMALIAN CELL LINE EXPRESSING INDUCIBLE C-SRC

(75) Inventor: Naoto Yamaguchi, Chiba (JP)

(73) Assignee: National University Corporation Chiba University, Chiba (JP)

(*) Notice: Subject to any disclaimer, the term of this patent is extended or adjusted under 35 U.S.C. 154(b) by 809 days.

(21) Appl. No.: 12/333,652

(22) Filed: Dec. 12, 2008

(65) Prior Publication Data

US 2009/0155901 A1   Jun. 18, 2009

Related U.S. Application Data

(60) Provisional application No. 61/013,099, filed on Dec. 12, 2007.

(51) Int. Cl.
*C12N 5/00* (2006.01)
*C07H 21/04* (2006.01)

(52) U.S. Cl. ...................... 435/325; 536/23.5

(58) Field of Classification Search ................ None
See application file for complete search history.

(56) References Cited

U.S. PATENT DOCUMENTS

2003/0032596 A1* 2/2003 Schneider et al. .............. 514/12
2006/0251734 A1* 11/2006 Kufe et al. .................... 424/649

OTHER PUBLICATIONS

Leu et al in "Lipopolysaccharide-induced c-Src expression plays a role in nitric oxide and TNFα secretion in macrophages" (Molecular Immunology, vol. 43, pp. 308-316; available online May 24, 2005).*
Kuga et al in "Differential mitotic activation of endogenous c-Src, c-Yes, and Lyn in HeLa cells", Archives of Biochemistry and Biophysis vol. 466, pp. 116-124, available online Jul. 14, 2007).*

* cited by examiner

*Primary Examiner* — Nancy T Vogel
*Assistant Examiner* — Catherine Hibbert
(74) *Attorney, Agent, or Firm* — Kilyk & Bowersox, P.L.L.C.

(57) ABSTRACT

The present invention is directed to a unique mammalian cell line expressing inducible c-Src, and, particularly, a unique human cell line overexpressing c-Src in an inducible manner.

4 Claims, 13 Drawing Sheets

MAMMALIAN CELL LINE EXPRESSING INDUCIBLE C-SRC

Figure 1:
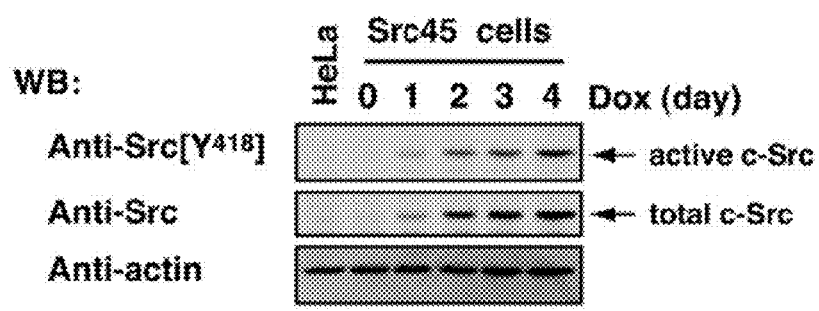
Figure 1:
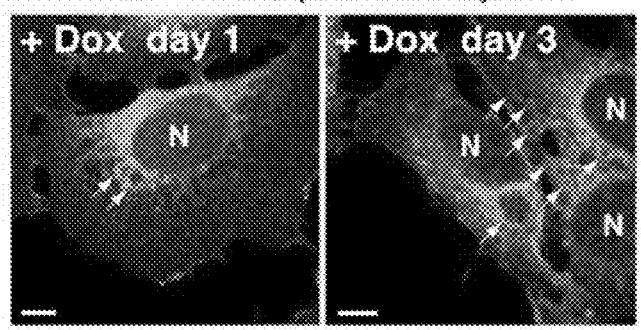
Figure 1:
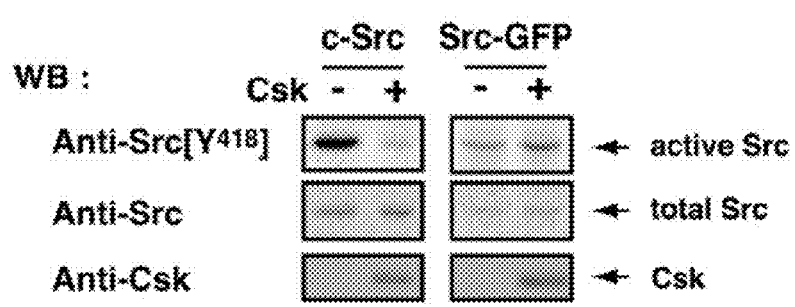
Figure 1:
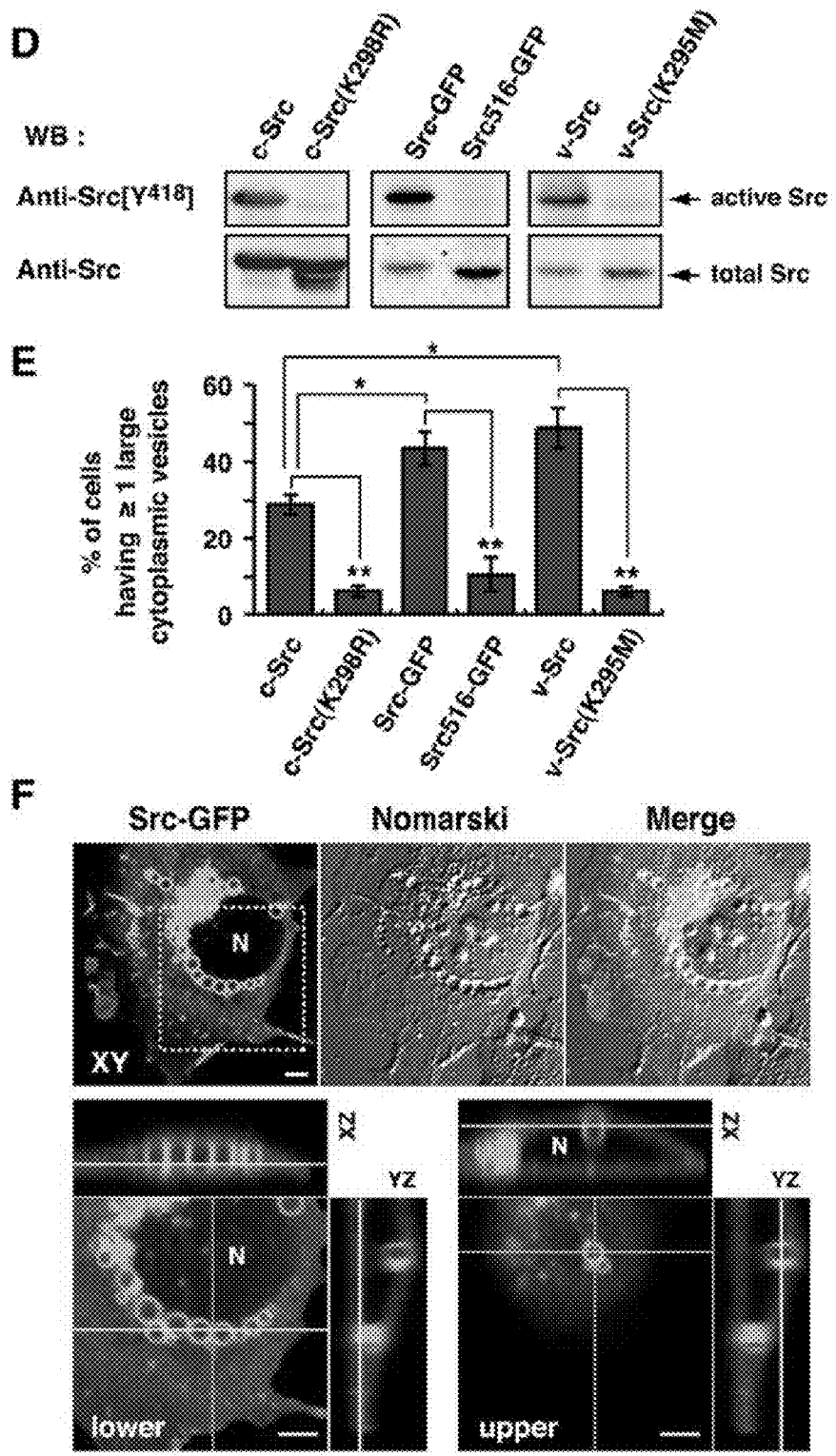

This application claims the benefit under 35 U.S.C. §119 (e) of prior U.S. Provisional Patent Application No. 61/013, 099, filed Dec. 12, 2007, which is incorporated in its entirety by reference herein.

BACKGROUND OF THE INVENTION

1. Field of the Invention

The present invention relates generally to a unique mammalian cell line expressing inducible c-Src, and, particularly, a unique human cell line overexpressing c-Src in an inducible manner.

2. Description of the Related Art

Macropinocytosis enables nonselective uptake of solute macromolecules, including nutrients and antigens, from the extracellular milieu through formation of clathrin-independent large (>1 μm in diameter) vesicles of irregular size (Swanson and Watts, 1995; Cardelli 2001; Conner and Schmid, 2003). Although high macropinocytic activity is observed in phagocytes such as macrophages and dendritic cells, most cells do not exhibit macropinocytic activity under normal culture conditions (Swanson and Watts, 1995). Some cell types show remarkable macropinocytosis after stimulation with growth factors, such as macrophage colony-stimulating factor (M-CSF) and epidermal growth factor (EGF) (Racoosin and Swanson, 1993; Hewlett et al., 1994), or mitogens such as phorbol 13-myristate 12-acetate (PMA) (Swanson, 1989; Sun et al., 2003; Sun and Endo, 2005).

Macropinosomes are generated from sites of membrane ruffling, which can take two forms: cell edge ruffling and dorsal surface ruffling (Swanson and Watts, 1995; Araki et al., 1996; Ellerbroek et al., 2004). After formation and subsequent budding, macropinosomes mature differently in different cell types. In macrophages, they mature with centripetal movement and shrinkage accompanied by a change in composition; a newly formed macropinosome begins as an early endosome derived from the plasma membrane, rapidly matures into a late endosome, and then merges with the lysosomal compartment, which is the end point of macropinocytosis (Racoosin and Swanson, 1992, 1993; Swanson and Watts, 1995). Unlike macrophages, in EGF-stimulated human epidermoid carcinoma A431 cells. macropinosomes are recycled back to the cell surface without fusing with lysosomes (Hewlett et al., 1994). However. little is known about how different macropinosomal maturation processes are regulated.

Src-family tyrosine kinases (SFKs), which are nonreceptor-type tyrosine kinases, consist of proto-oncogene products and structurally related proteins and include at least eight highly homologous proteins: c-Sre, Lyn, Fyn, c-Yes, c-Fgr, Hck, Lck, and Blk. SFKs regulate cell proliferation, migration, and cytoskeletal reorganization (Brown and Cooper, 1996; Thomas and Brugge, 1997). They also control membrane trafficking, such as endocytic internalization of the EGF receptor (EGFR), early endosomal dynamics, and organization of the Golgi apparatus to transport proteins to the ER (Ware at al., 1997; Bard et al., 2003; Gasman et al., 2003).

SFKs exhibit four highly conserved Src homology (SH) domains: an N-terminal SH4 domain (followed by a poorly conserved "Unique" domain), an SH3 domain, an SH2 domain, and an SH1 tyrosine kinase domain (Brown and Cooper, 1996, Thomas and Brugge, 1997). The SH4 domain contains the signal(s) for acylation, such as N-myristoylation and palmitoylation, and regulates association with the cytoplasmic surface of membranes, while SH3 and SH2 domains mediate protein-protein interactions.

Given the high homology of SFKs. it is not surprising that their functions overlap. Although mice or cells deficient in multiple members of the SFK family display more severe defects than those lacking a single SFK (Stein et al., 1994; Thomas and Brugge, 1997; Bard et al., 2003), specific functions of single SFKs have been noted in knockout mice or cells (Thomas et at., 1995; Lowell et al., 1996; Thomas and Brugge, 1997). However, it is unclear how the functional specificity of a specific SFK is determined.

BRIEF SUMMARY OF THE INVENTION

The present invention relates generally to a unique mammalian cell line expressing c-Src.

In one embodiment, a unique human cell line overexpressing c-Src in an inducible manner is provided.

In another embodiment, a unique HeLa cell clone overexpressing c-Src in an inducible manner is provided.

These and other aspects of this invention will be apparent upon reference to the attached figures and following detailed description. To this end, various references are set forth herein, which describe in more detail certain procedures, compounds and/or compositions, and are incorporated by reference in their entirety.

Abbreviations: EGF, epidermal growth factor; FRAP, fluorescence recovery after photobleaching; GRP, green fluorescent protein; NEM, N-ethyl maleimide; PMA, phorbol 13-myristate 12-acetate; SFK, Src-family tyrosine kinase; SH, Src homology.

The accompanying drawings, which are incorporated in and constitute a part of this application, illustrate some of the embodiments of the present invention and together with the description, serve to explain the principles of the present invention.

BRIEF DESCRIPTION OF THE DRAWING(S)

FIG. 1 shows induction of large vesicles by c-Src expression. A, B: HeLa cells expressing inducible c-Src (Src45 cells) were cultured in the presence of doxycycline (Dox) for the indicated periods. (A) Equal amounts of lysates were analyzed by Western blotting with anti-Src[$Y^{418}$], anti-Src, and anti-actin (loading control) antibodies. (B) Immunostaining with anti-Src. Arrows indicate large vesicles associated with c-Src. C: COS-1 cells transfected with c-Src, c-Src plus Csk, Src-GFP, or Src-GFP plus were cultured for 1 day. Equal amounts of lysates were analyzed by Western blotting with anti-Src [$Y^{418}$], anti-Src, and anti-Csk antibodies. D, E: COS-I cells transfected with the indicated Src construct were cultured for 24 h. (D) Equal amounts of lysates were analyzed by Western blotting with anti-Src[$Y^{418}$] and anti-Src antibodies. (E) Cells exhibiting 1 or more large cytoplasmic vesicles were quantitated. Data represent means±SD from three independent experiments. Asterisks indicate significant differences (*$P<0.01$, **$P<0.001$) calculated by Student's t-test. F: COS-1 cells transfected with Src-GFP were cultured for 1 day, and live cells were imaged by GFP fluorescence and Nomarski optics. One planar (xy) section and magnified images of lower and upper sections of the squared area are shown and orthogonal sections viewing the axial direction (xz and yz) are created in the margins. Note that large vesicles associated with Src-GFP are clearly visualized by Nomarski optics. N, nucleus. Bars, 5 μm.

Figure 2:
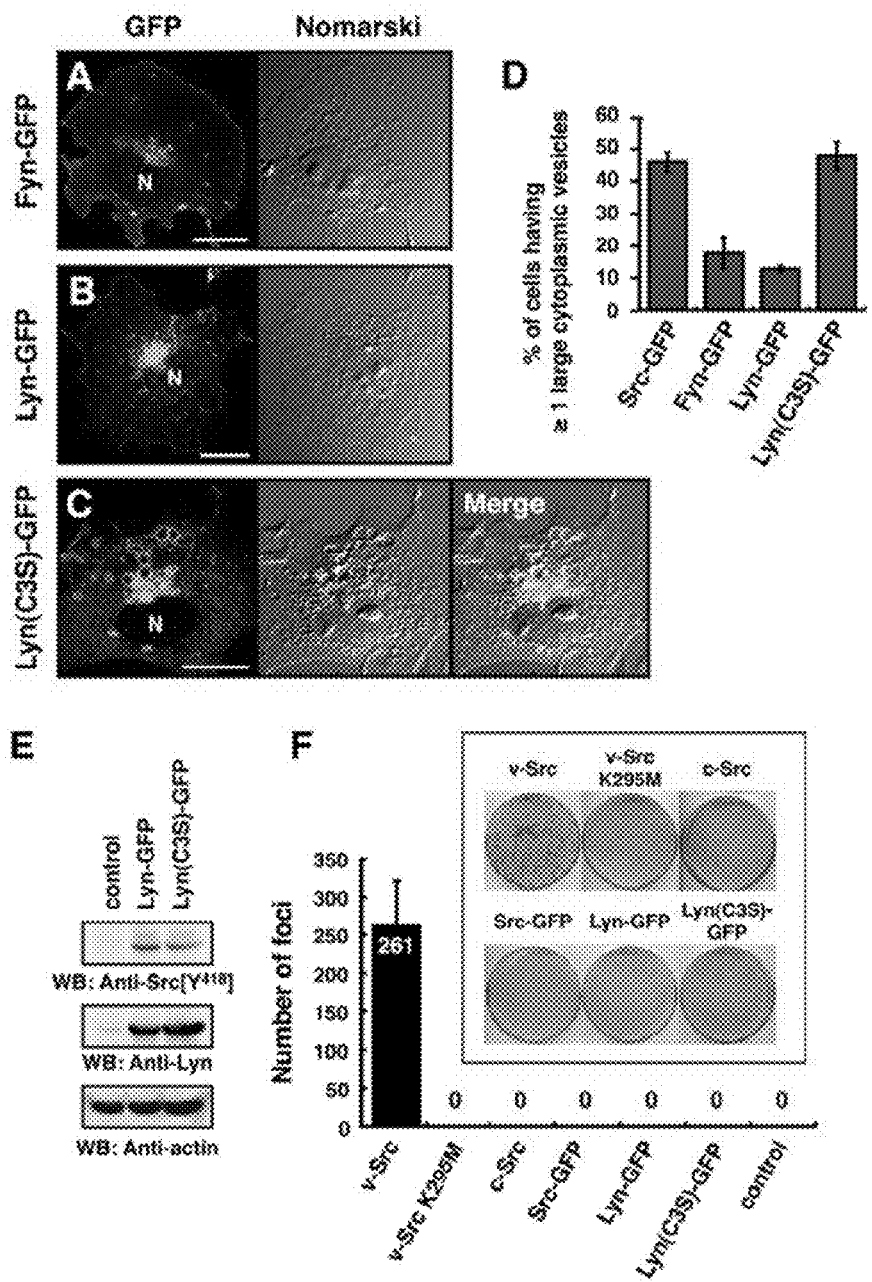

FIG. 2 shows formation of large vesicles by SFKs that are not palmitoylated. A-D: COS-1 cells transfected with Fyn- GFP (A), Lyn-GFP (B), and Lyn(C3S)-GFP (C) were cultured for 1 day. A-C: Large vesicles were detected by GFP fluorescence and Nomarski optics. N, nucleus. Bars, 20 µm. D: Cells exhibiting 1 or more large cytoplasmic vesicles were quantitated. Data represent means±D from three independent experiments. E: Equal amounts of lysates from COS-1 cells transfected with Lyn-GFP or Lyn(C3S)-GFP were analyzed by Western blotting with anti-Src($Y^{418}$], anti-Lyn, and anti-actin antibodies. F: Transformation assay. 10T½ cells were transfected with the indicated construct (5 µg), and after 12 days, the number of transformed foci was determined. Data represent means±SD from three independent experiments. Representative results are shown in the inset.

Figure 3:
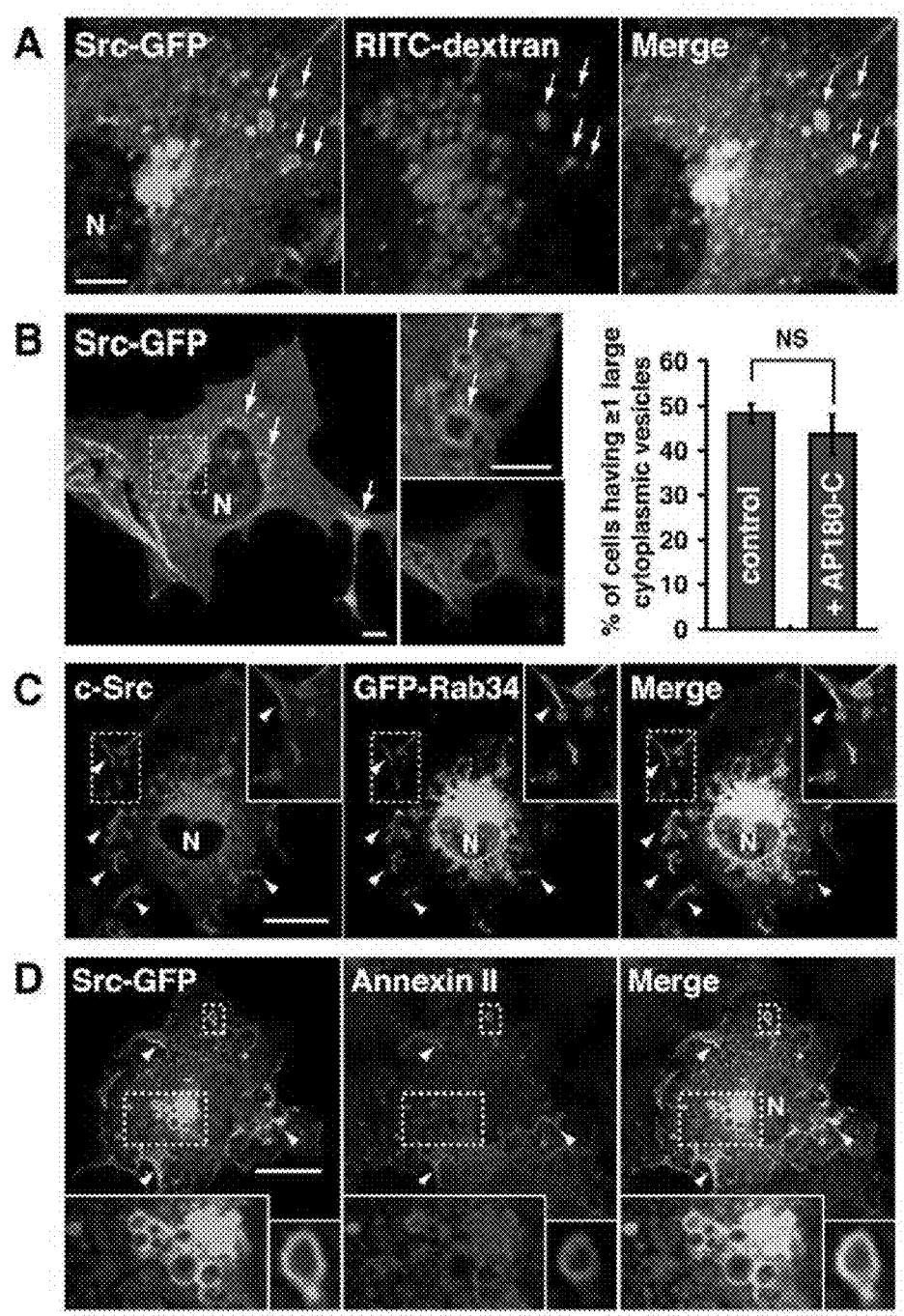
Figure 3:
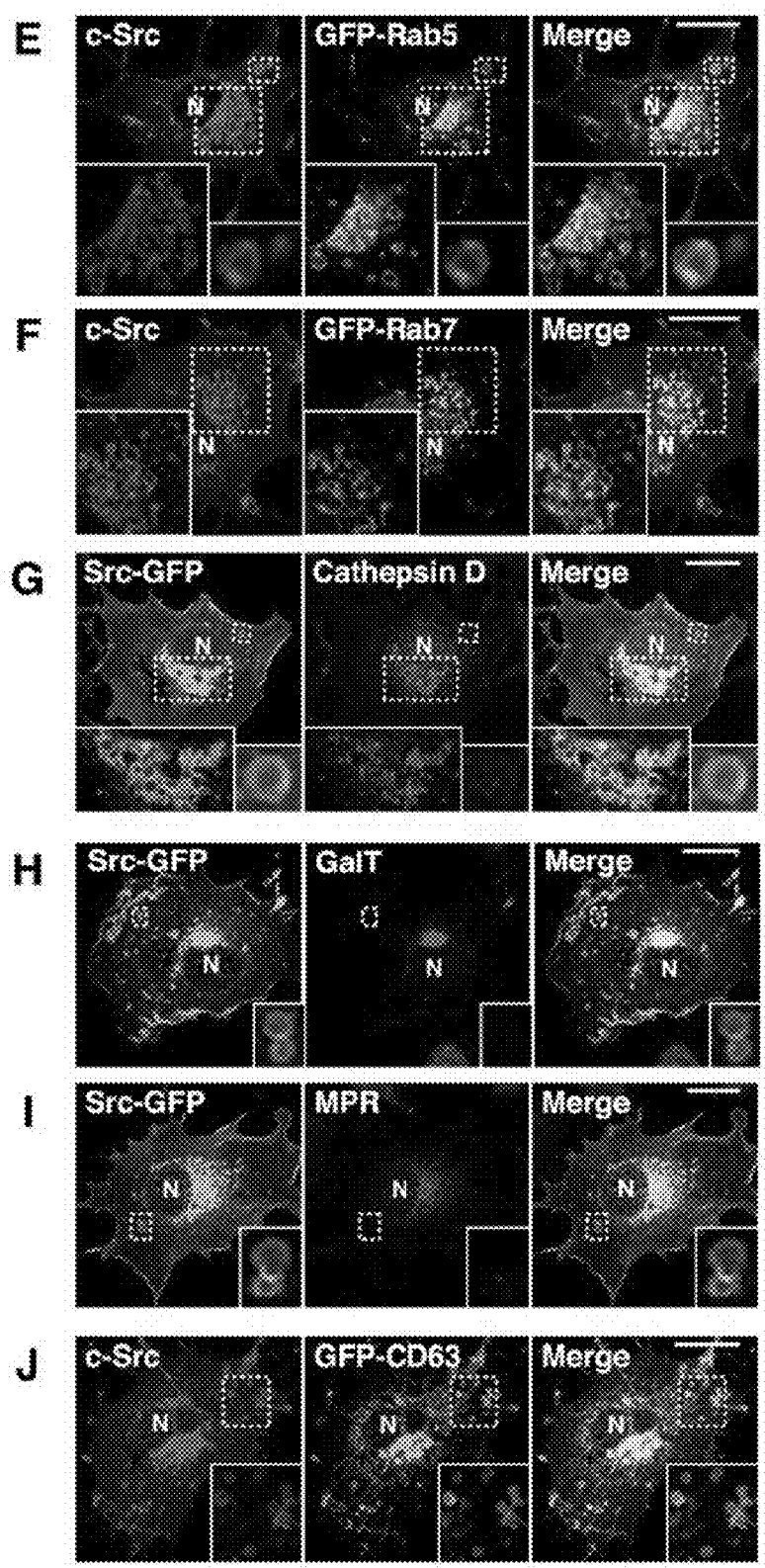

FIG. 3 shows c-Src-induced large vesicles constitute macropinosomes. A: COS-1 cells transfected with Src-GRP (green) were treated with 1 mg/ml RITC-dextran (red, Mr 70,000) for 3 h. Arrows indicate c-Src-associated large vesicles having taken up RITC-dextran. Bar, 5 µm. B: COS-1 cells co-transfected with Src-GFP (green) plus myc-AP180-C (red) were cultured for 24 h. Squared areas are magnified. Arrows indicate independent experiments. The difference between Src-GRP (control) and Src-GFP plus myc-AP180-C (+AP180-C) was not significant (NS), as calculated by Student's t-test. C-J: COS-1 cells transfected with c-Src plus GFP-Rab 34 (C), Src-GFP alone (D, G-I), c-Src plus GFP-Rab5 (E), c-Src plus GFP-Rab 7 (F), and c-Src plus GFP-CD63 (J) were cultured for 1 day, and expressed proteins were detected with GFP fluorescence (green), or anti-Src (red, C,E,F, and J), anti-annexin II (red, D), anti-cathepsin D (red, G), anti-galactosyltransferase (GalT; red, H) and anti-mannose-6-phosphate receptor (MPR; red, I) antibodies. All Z-series sections at 0.5-µm intervals were merged in two-dimensional xy images. Arrowheads indicate co-localization of c-Src with Rab34 or annexin II at membrane ruffles. Magnified images of squared areas are shown in insets. Bars, 20 µm, N, nucleus.

Figure 4:
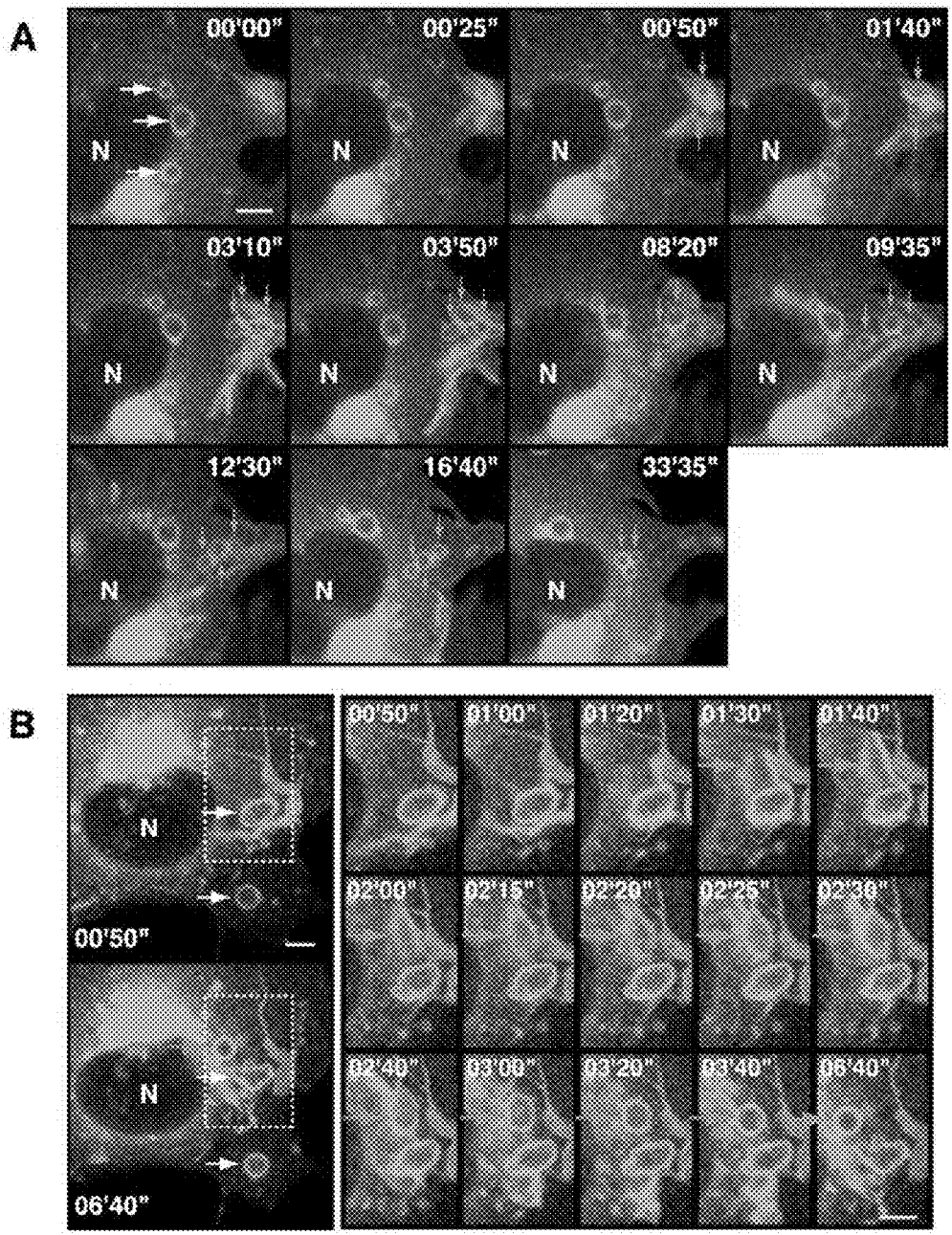
Figure 4:
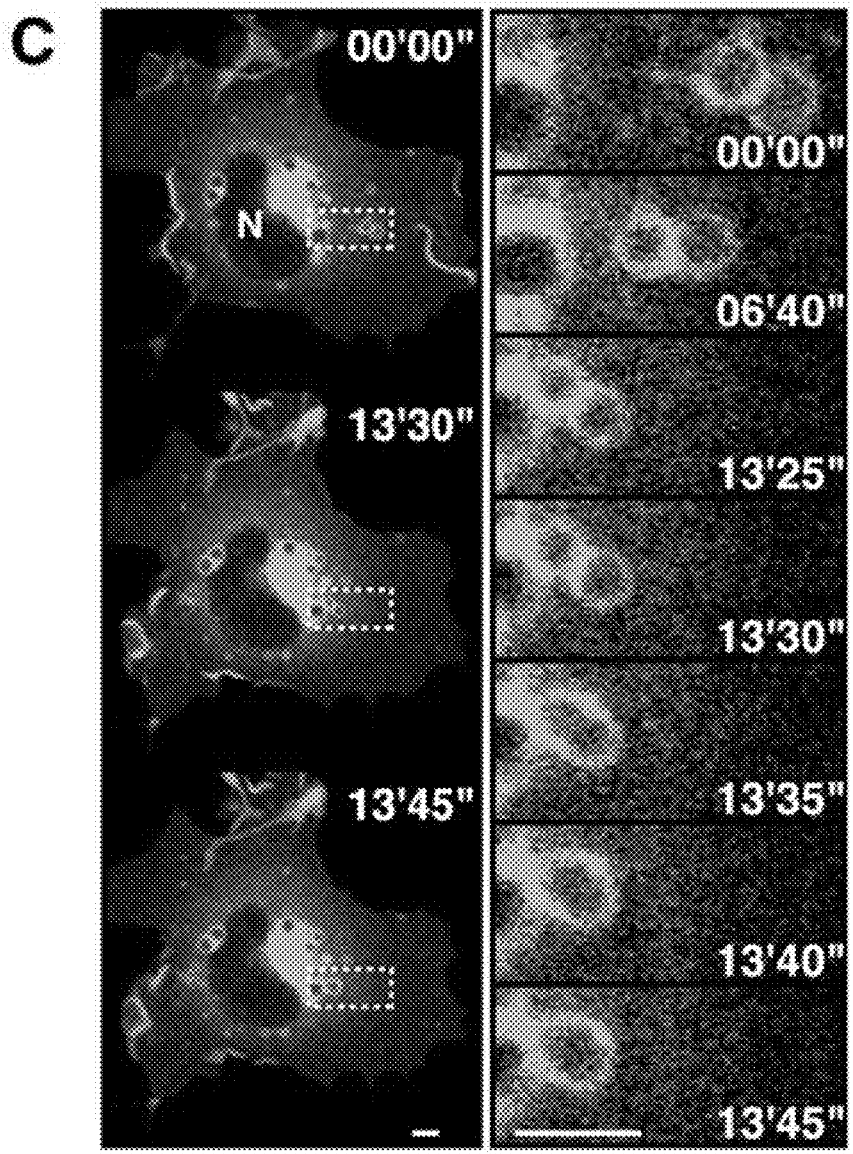

FIG. 4 shows biogenesis and trafficking of macropinosomes in living cells. Living COS-1 cells expressing Src-GFP were monitored by GFP fluorescence at 5-sec intervals. A, B: Biogenesis of macropinosomes from peripheral ruffles (A) and dorsal-surface ruffles (B). White and red arrows indicate macropinosomes that had already formed when monitoring began and those newly formed during the monitoring period, respectively. Magnified images are shown on the right (B). Note that Src-GFP-associated macropinosomes rapidly formed from membrane ruffles and then slowly moved centripetally, decreasing in size. C: Two macropinosomes moved centripetally (00'00"-13'25") and then fused (13'30"-13'45"). Magnified images of the squared area are aligned on the right. The starting of time-lapse monitoring is indicated as 0 sec (00'00"). N, nucleus. Bars, 5 µm.

Figure 5:
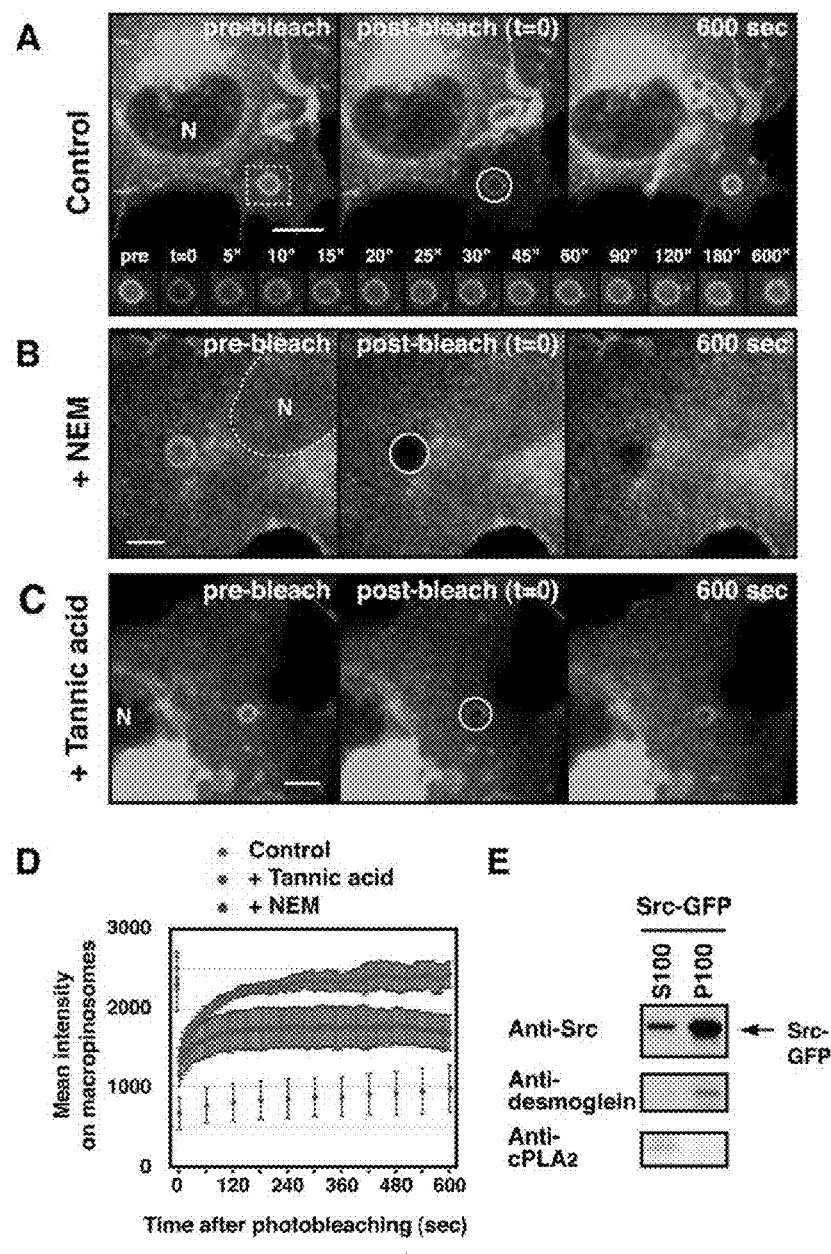

FIG. 5 shows FRAP of Src-GFP on macropinosomes. A-D: FRAP analysis of Src-GFP was performed in COS-I cells treated with cycloheximide. Cells expressing Src-GFP were pretreated with nothing (control) (A), 1 mM NEM (B), or 0.5% tannic acid (C) for 10 min. Enclosed areas (yellow circles) were photobleached and cells were monitored at 5-sec (A and C) or 60-sec intervals (B) for 10 min. Mean fluorescence intensities on macropinosomes were measured, and results are means±SD (control, n=4; NEM, n=3; Tannic acid, n=5). N, nucleus. Bars 5 µm. E: Equal amounts of lysates from S100 and P100 fractions of Src-GFP-expressing COS-I cells were analyzed by Western blotting with anti-Src, anti-cPLA$_2$ (cytosol marker), and anti-desmoglein (plasma membrane marker) antibodies.

Figure 6:
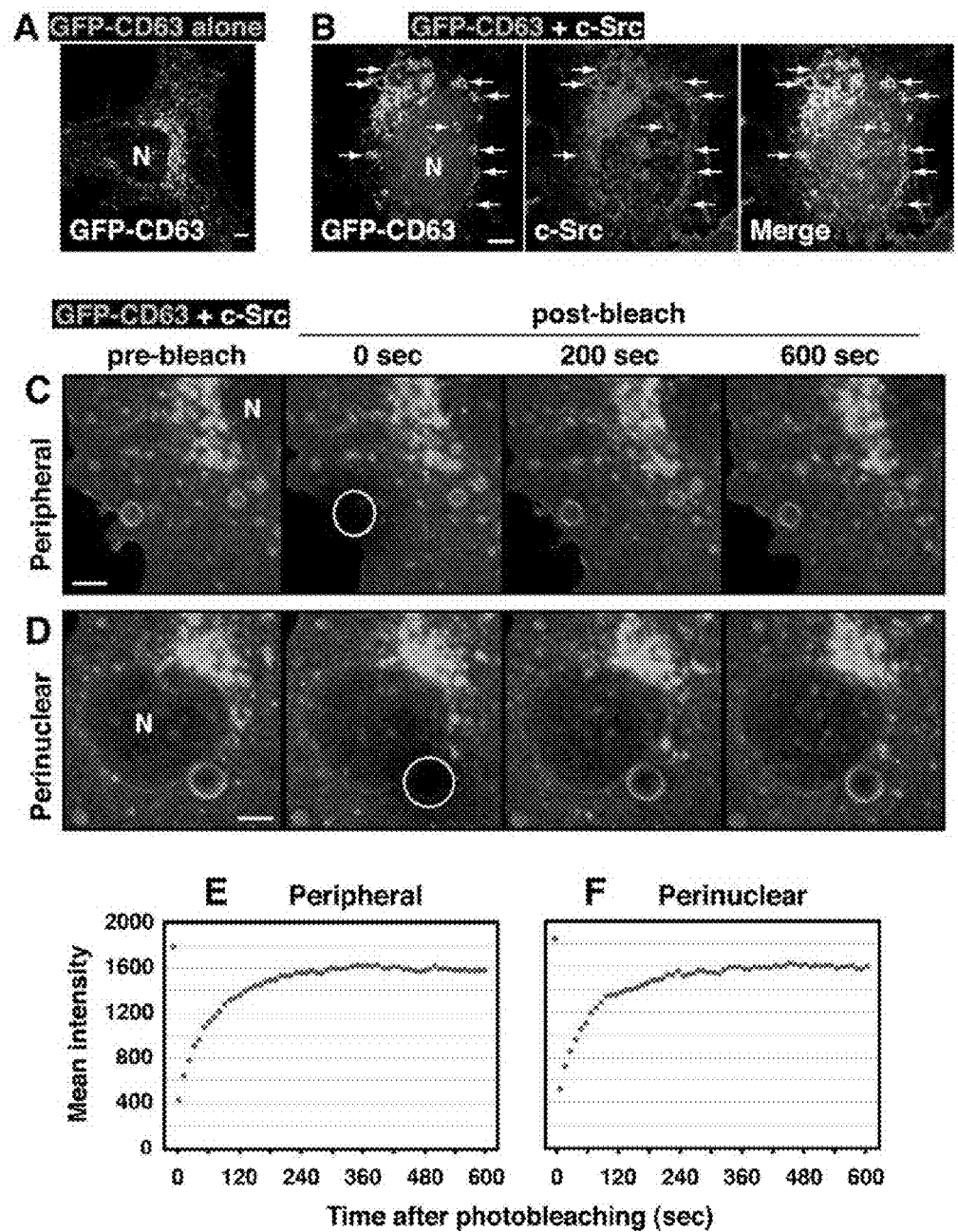

FIG. 6 shows FRAP of GFP-CD63 on c-Src-induced macropinosomes. A, B: COS-I cells transfected with GFP-CD63 (A) and GFP-CD63 plus c-Src (B) were cultured for I day and analyzed for GFP fluorescence (green) and anti-Src (red, B) positivity. Arrows indicate macropinosomes associated with CD63 and c-Src, C-F: GFP-CD63 FRAP experiments were performed in cycloheximide-treated COS-I cells expressing GFP-CD63 and c-Src. Enclosed areas on macropinosomes appearing at peripheral (C and E) and perinuclear (D and F) regions were photobleached, and cells were monitored at 5-sec intervals for 10 min. Mean fluorescence intensities on macropinosomes were measured, and representative results are shown in parts E and F. Note that the kinetics of fluorescence recovery of GFP-CD63 in peripheral and perinuclear macropinosomes was similar to that of Src-GFP (see FIG. 4D, control). N, nucleus. Bars, 5 µm.

Figure 7:
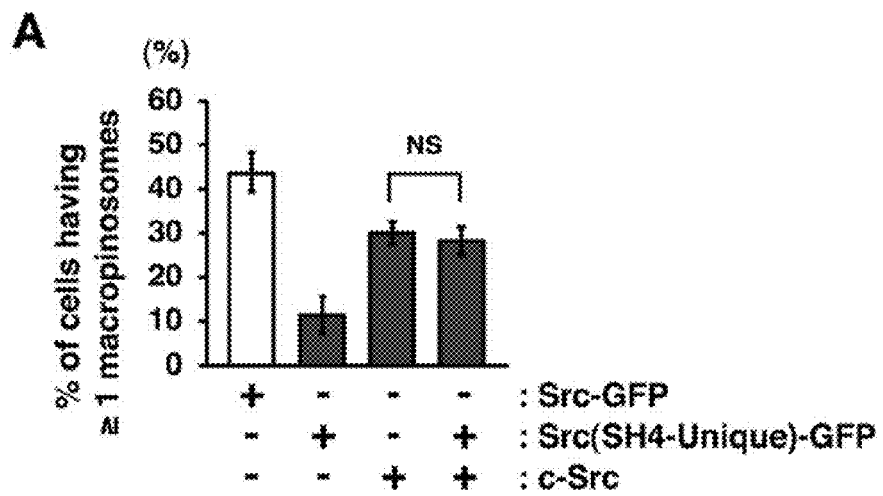
Figure 7:
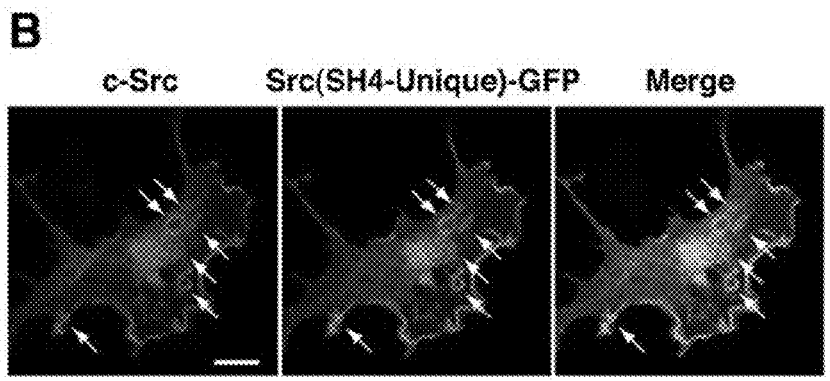
Figure 7:
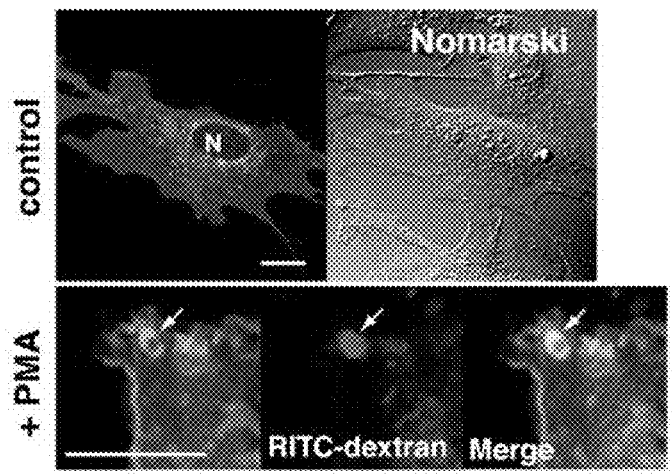
Figure 7:
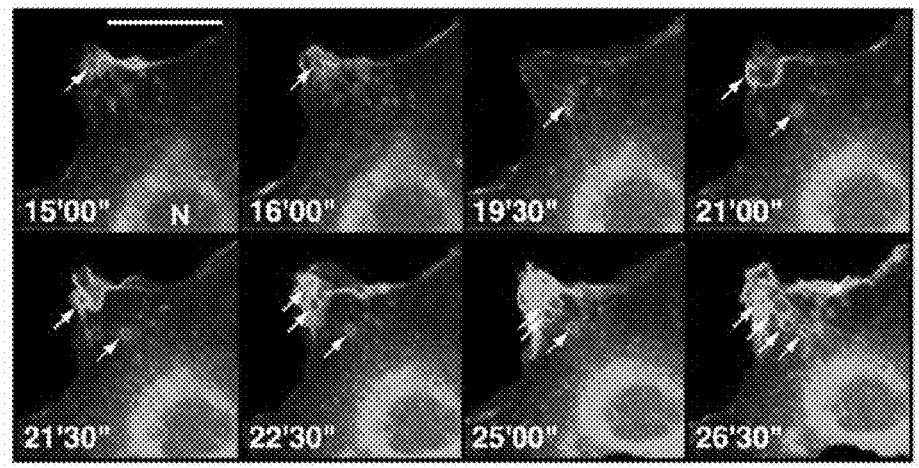
Figure 7:
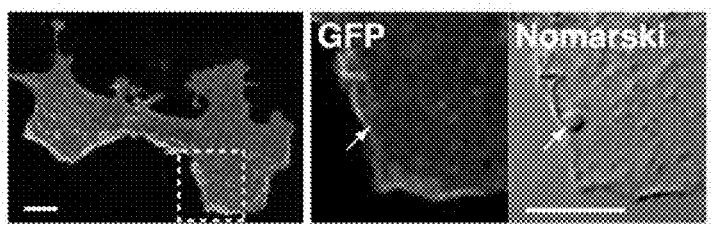
Figure 7:
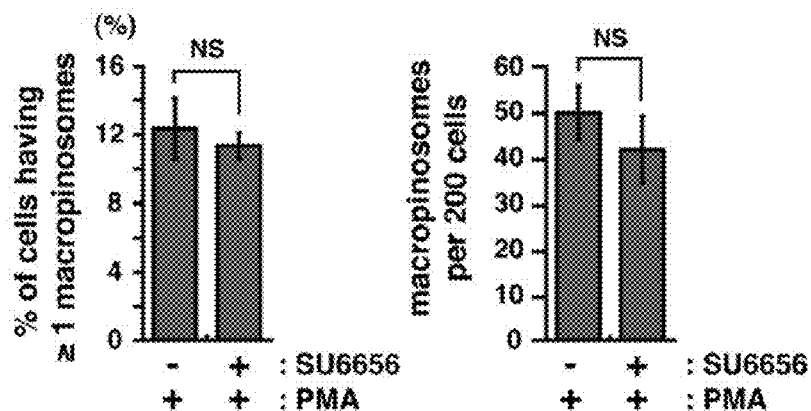

FIG. 7 shows association of the c-Src N-terminus with macropinosomes. A: COS-I cells transfected with the indicated construct were cultured for 24 h, and cells exhibiting I or more macropinosomes were quantitated. Data represent means±SD from three independent experiments. The difference between c-Src alone and c-Src plus Src(SH4-Unique)-GFP was not significant (NS), as calculated by Student's t-test. For comparison, the open bar is a reproduction of the data of Src-CFP in FIG. 2D. B: COS-1 cells transfected with c-Src plus Src(SH4-Unique)-GFP were cultured for 24 h and visualized with anti-Src (red) immunofluorescence and GFP fluorescence (green). C: 10T½ cells transfected with Src (SH4-Unique)-GFP (control) were treated with 200 nM PMA plus 1 mg/ml RITC-dextran for 15 min (1 PMA). D: 10T½ cells expressing Src(SH4-Unique)-GFP were stimulated with 200 nM PMA and cells were monitored at 30-sec intervals. The time of PMA addition is indicated as 0 sec (00'00"). E: 10T½ cells expressing Lyn(SH4-Unique)-GFP were treated with 200 nM PMA for 30 min and imaged by GFP fluorescence and Nomarski optics. F: 10T½ cells were pretreated with 5 µM SU6656 or none for 30 min and then stimulated with 200 nM PMA plus 1 mg/ml RITC-dextran for 20 min. Cells exhibiting one or more macropinosomes labeled with RITC-dextran (left) were quantitated, and the number of macropinosomes per 200 cells is shown on the right. Data represent means±SD from three independent experiments. The difference between PMA alone and PMA plus SU6656 was not significant (NS), as calculated by Student's t-test. Arrows indicate macropinosomes. N, nucleus. Bars, 10 µm.

Figure 8:
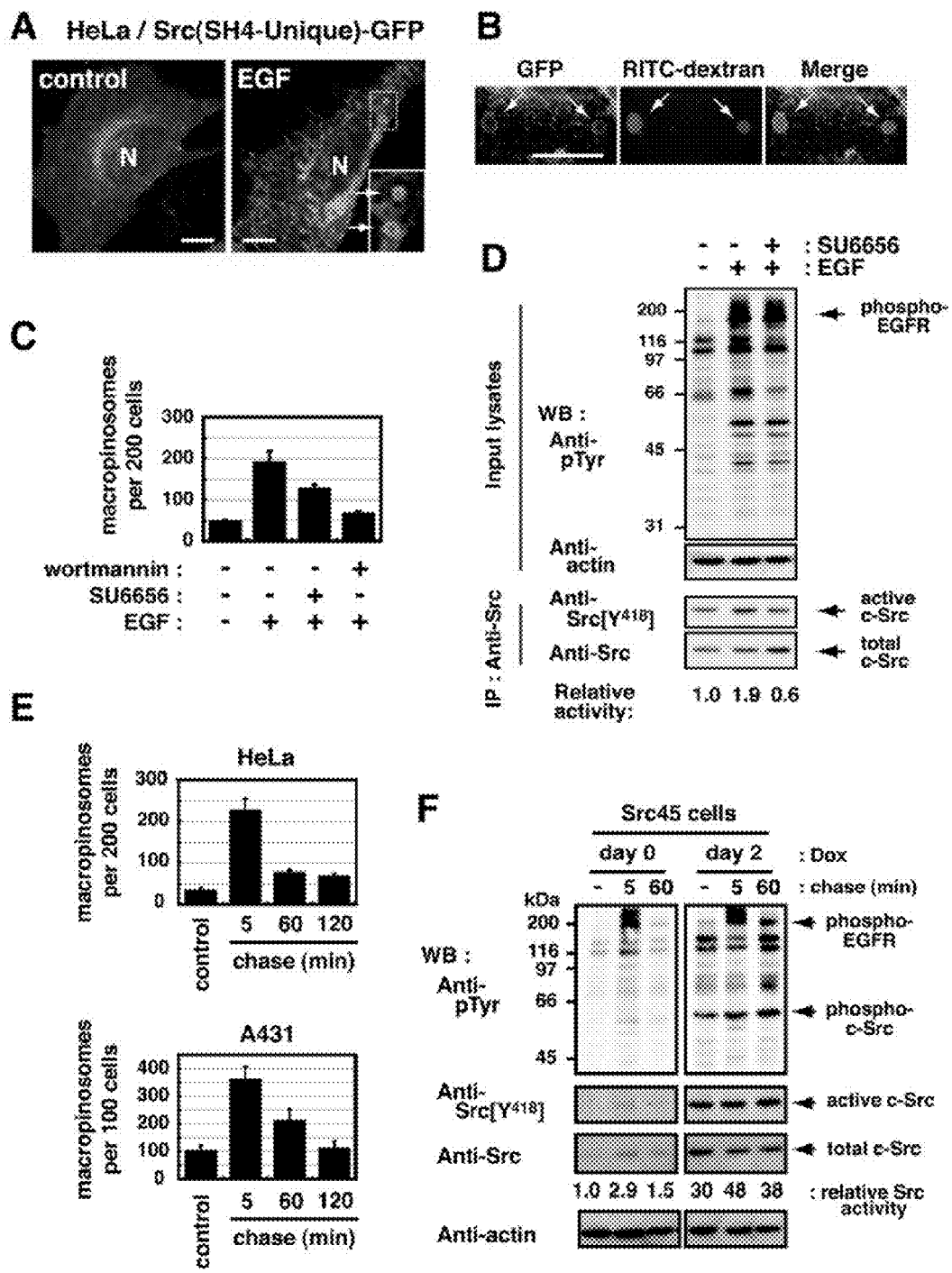
Figure 8:
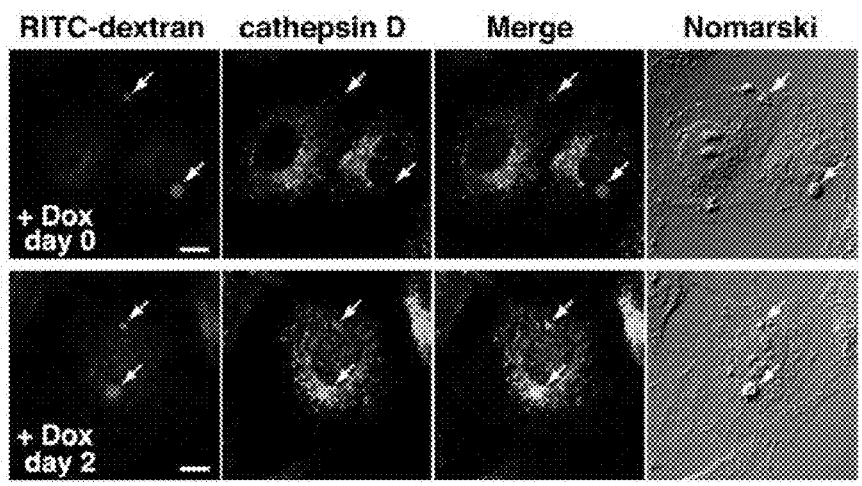
Figure 8:
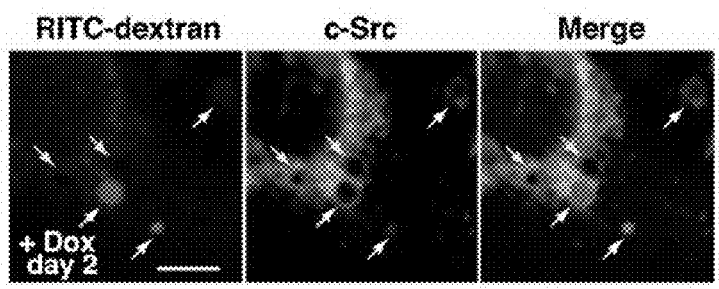
Figure 8:
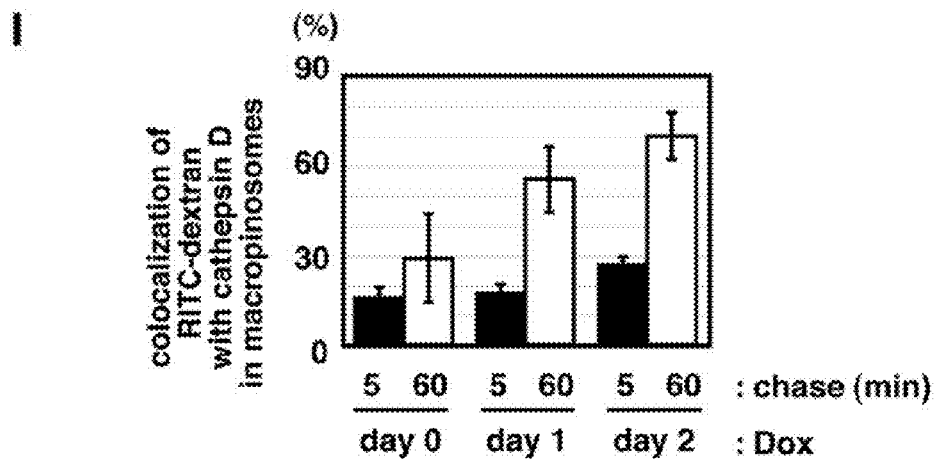

FIG. 8 shows Involvement of c-Src in maturation of EGF-induced macropinosomes. A-C: Serum-starved HeLa cells expressing Src(SH4-Unique)-GFP (control) were stimulatad for 15 min with 50 ng/ml EGF and visualized by GFP fluorescence (A). During stimulation, cells were treated with 1 mg/ml RITC-dextran (B). White arrows indicate macropinosomes. C: Cells were pretreated for 30 min with 5 µM SU6656 or 200 nM wortmannin and then stimulated with EGF for 15 min. The number of macropinosomes associated with Src(SH4-Unique)-GFP per 200 cells is shown. Data represent means±SD from three independent experiments. D: Serum-starved HeLa cells were pretreated with 5 µM SU6656 or none and stimulated with EGF for 15 min. Equal amounts of lysates (input lysates) were analyzed by Western blotting with anti-pTyr and anti-actin antibodies. c-Src immunoprecipitates from lysates were analyzed by Western blotting with anti-Src[$Y^{418}$] and anti-Src antibodies. c-Src kinase activity was quantitated by measuring signal intensity using anti-Src [$pY^{418}$] antibody and normalized to the corresponding signal intensity detected by anti-Src. Results are expressed as mean values (fold) relative to the specific activity of c-Src in unstimulated control cells. E: Serum-starved HeLa and A431 cells expressing Src(SH4-Unique)-GFP were treated with EGF for 5 min., washed twice with serum-free medium, and cultured in serum-free medium (chase) for the indicated periods. The number of Src:(SH4-Unique)-GFP-labeled macropinosomes per 200 HeLa (left) or 100 A431 (right) cells was counted. Data represent means±SD from three independent experiments. F-I: Src45 cells cultured in medium containing Dox for 0-2 days were stimulated with EGF for 5 min after serum starvation and chased for indicated periods. F: Lysates were analyzed by Western blotting with anti-Src[$Y^{418}$], anti-Src, anti-pTyr, and anti-actin antibodies. Relative c-Src kinase activity is shown, as described in D. G-I: Src45 cells cultured for 2 days in the presence or absence of Dox were treated with RITC-dextran (red) during 5 min of EGF stimulation, chased for 60 min, and stained with anti-cathepsin D (G, green) or anti-Src (H, green) antibodies. White arrows indicate macropinosomes containing RITC-dextran. Yellow arrows indicate c-Src-associated large vesicles negative for RITC-dextran. This result suggests continuous macropinocytosis during the 60-min chase period since the morphology of the large vesicles is similar to RITC-dextran-labeled macropinosomes. I: Co-localization of RITC-dextran with cathepsin D in macropinosomes was quantitated. Data represent means±SD from three independent experiments. Bars, 10 μm. N, nucleus.

DETAILED DESCRIPTION OF THE INVENTION

The present invention relates generally to a unique mammalian cell line expressing inducible c-Src, designated as the Src45 cell line for purposes herein. In one aspect, a unique human cell line overexpressing c-Src in an inducible manner, such as the Src45 cell line, is provided. In another aspect, a unique HeLa cell clone overexpressing c-Src in an inducible manner, such as the Src45 cell line, is provided.

Src-family kinases that localize to the cytoplasmic side of cellular membranes through lipid modification play a role in signaling events including membrane trafficking. Macropinocytosis is an endocytic process for solute uptake by large vesicles called macropinosomes. Although macropinosomes can be visualized following uptake of fluorescent macromolecules, little is known about the dynamics of macropinosomes in living cells. Here, we show that constitutive c-Src expression generates macropinosomes in a kinase-dependent manner. Live-cell imaging of GFP-tagged c-Src (Src-GFP) reveals that c-Src associates with macropinosomes via its N-terminus continuously from their generation at membrane ruffles, through their centripetal trafficking, to fusion with late endosomes and lysosomes. Fluorescence recovery after photobleaching (FRAP) of Src-GFP shows that Src-GFP is rapidly recruited to macropinosomal membranes from the plasma membrane and intracellular organelles through vesicle transport even in the presence of a protein synthesis inhibitor. Furthermore, using a HeLa cell line overexpressing inducible c-Src, we show that following stimulation with epidermal growth factor (EGF), high levels of c-Src kinase activity promote formation of macropinosomes associated with the lysosomal compartment. Unlike c-Src, Lyn and Fyn, which are palmitoylated Src kinases, only minimally induce macropinosomes, although a Lyn mutant in which the palmitoylation site is mutated efficiently induces macropinocytosis. We conclude that kinase activity of nonpalmitoylated Src kinases including c-Src may play an important role in the biogenesis and trafficking of macropinosomes.

The present invention may be better understood by reference to the following non-limiting Examples which are provided as exemplary of the invention.

EXAMPLES

In this study, we investigated the activity of SFKs in biogenesis and trafficking of macropinosomes by live-cell imaging and fluorescence recovery after photobleaching (FRAP). Our results indicate that c-Src associates with macropinosomes from their generation to their fusion with lysosomes and thus, may play a continuous role in their activity.

Materials and Methods

Plasmids cDNA encoding human c-Src (1-536; with I designating the initiator methionine) (kindly provided by D. J. Fujita; Bjorge et al., 1995) was amplified by PCR using the sense primer 5'-AAAGAATTCCGACCATGGGTAGCAA-3' (SEQ ID No:2) and the antisense primer 5'-TTTCTC-GAGCTGTGCCTAGAGGTTCTCCC-3' (SEQ ID No:3), Src-GFP (1-532), Src516-GFP (1-516), and Src(SH4-Unique)-GFP were constructed by fusion with GFP obtained from the pEGFP-CI (Clontech, Mountain View, Calif.) vector. Human Lyn (kindly provided by T. Yamamoto Yamanashi et at., 1987) and Lyn-GFP were described previously (Kasahara et al., 2004). The Cys→Ser mutation at position 3 [Lyn (C3S)] was generated by site-directed mutagenesis using the sense primer 5'-CACCGCGAGCGGGAAATATGGGATC-GATAAAATCAAAAGGG-3' (SEQ ID No:4) and the antisense primer 5'-CCCTTTTGATTTTATCGATC-CCATATTTCCCGCTCGCGG-TG-3' (SEQ ID No:5). Lyn (SH4-Unique)-GFP (1-62) was amplified by PCR using the sense primer 5'-AAACACGCGTCGAGCGG-GAAATATGGGATGT-3' (SEQ ID No:6) and the antisense primer 5'-CCAAAGTTTGATTTCTAGGTCTCCACCG-GTAAGA-3' (SEQ ID No:7). The resulting fragments were confirmed by sequencing. Fyn-GFP (1-523) was constructed from cDNA for human Fyn (1-536) (a kind gift of T. Yamamoto; Tezuka et al, 1999) by fusion with GFP. Rat Csk cDNA was provided by M. Okada and S. Nada (Nada et al., 1991). All constructs were subcloned into the pcDNA4/TO vector (Invitrogen, Carlsbad, Calif.). Human c-Src(K298R) subcloned into pcDNA3 (Invitrogen) was provided by S. A. Laporte (Fessart et al., 2005). Chicken v-Src and v-Src (K295M) subdoned into pcDNA3 were provided by H. Ohnishi (Ohnishi et at., 2001). GFP-tagged mouse Rab34 was constructed as described (Sun et al., 2003). cDNAs encoding dog Rab7 (Bucci et al., 2000), human Rab5a (Rosenfeld et al., 2001), and human CD63 (Blott et al., 2001) subcloned into pEGFP-CI were provided by B. van Deurs, B. J. Knoll, and G. M. Grjffiths, respectively. cDNA encoding N-terminally myc-tagged rat AP180-C (the C-terminal residues 530-915 of AP180; Snyers et al., 2003) subcloned tnto pCI (Promega, Madison, Wis.) was a gift of L Snyers.

The sequence listing of c-Src subcloned into pcDNA4/TO is represented by SEQ ID No:1, which is appended and included with this application.

Antibodies

The following antibodies were used: Src (#327; Oncogene), phosphotyrosine (pTyr, 4G10; Upstate Biotechnology, Charlottesville. Va.). Csk (#52; BD Transduction, San Jose, Calif.), annexin II (clone 5; BD Transduction), desmoglein (#62; BD Transduction), actin (CHEMICON, San Diego, Calif.). Src[$Y^{418}$] (phospho-Src-family, BioSource, Carlsbad, Calif.). cPLA$_2$ (N-216; Santa Cruz Biotechnology, Santa Cruz, Calif.), galactosyltransferase (GalT) (Yamaguchi and Fukuda, 1995), myc (A-14; Santa Cruz Biotechnology) (provided by M. N. Fukuda), cathepsin D (DAKO), and cation-dependent mannose 6-phosphate receptor (MPR) (Umeda et al., 2003; kindly provided by Y. Tanaka). HRP-F(ab')$_2$ secondary antibodies were from Amersham, Buckinghamshire, UK; FITC- or TRITC-F(ab')$_2$ secondary antibodies were from BioSource and Sigma-Aldrich, St Louis, Mo.

Cells and Transfection

COS-I, HeLa (Japanese Collection of Research Bioresources, Osaka, Japan). A43I, and mouse C3H/10T ½ fibroblast (Sun et al., 2003) cells were cultured in Iscove's modified DME containing 5% fetal bovine serum (FBS). Transfection was performed using TransIT transfection reagent (Mirus, Madison, Wis.) (Kasahara et al., 2004; Nakayama and Yamaguchi, 2005).

Src45 Cell Line

The CAG promoter-driven pCAG-TR vector expressing the tetracycline repressor (TR) was constructed from pcDNA6/TR (Invitrogen) by subcloning into the pCAG vector (provided by J. Miyazaki; Miyazaki et al., 1989). A HeLa cell clone co-transfected with pCAG-TR (clone #3-2) and a plasmid containing the hygromycin-resistance gene was selected in medium containing 5% FBS and 200 µg/ml hygromycin B (Wako Pure Chemicals, Osaka, Japan). TR expression in clone #3-2 was approximately eightfold higher than that seen in T-REx™-HeLa calls (Invitrogen), when examined by Western blotting using anti-TR antibody (Invitrogen) (data not shown). The Src45 cell line was generated from clone 3-2 by transfection with pcDNA4/TO (Invitrogen) expressing c-Src and selection in medium containing 5% FBS and 333 µg/ml Zeocin (Invitrogen). Doxycycline (Dox) was used at 2 µg/ml to induce c-Src.

Macropinosome Analysis

Macropinosomes wider than 2 µm labeled by c-Src or mutants were counted. All values were expressed as means±D from three independent experiments. Rhodamine B-isothiocyanate (RITC)-dextran (Mr 70,000), PMA, and wortmannin were from Sigma-Aldrich. SU6656 (Blake et al., 2000) was from Calbiochem. EGF was a kind gift of M. N. Fukuda. To induce macropinocytosis by EGF stimulation, cells were serum-starved for 12-18 h before treatment with 50 ng/ml EGF.

Transformation Assay

10T ½ cells ($3 \sim 7 \times 10^5$) were seeded in 100-mm dishes, and exponentially growing cells were transfected with the indicated c-DNA construct (5 µg). After 12 days, cells were fixed with methanol for 10 min, stained with 5% Giemsa solution for 45 min, and foci were counted.

Immunofluorescence

Immunofluorescence was performed using Fluoview FV500 (Olympus, Tokyo, Japan) with a 40×1.00 NA oil or a 60×1.00 water-immersion objective as described (Yamaguchi and Fukuda, 1995: Mera et al., 1999; Tada et al., 1999: Yamaguchi et al., 2001; Kasahara et al., 2004; Nakayama et al., 2006). For annexin II staining, cells were fixed in 100% methanol at −30° C. for 1 min after removal of medium.

Live-Cell Imaging

For live-cell imaging, cells cultured in 35-mm glass-based dishes were transiently transfected with plasmid DNA on the preceding day. Time-lapse monitoring was performed using a Fluoview FV5OO with a 40×1.00 oil objective. Images were obtained at low power laser (0.3-3.0% laser) using the 488 nm line of an argon laser. FRAP was performed as described (Kasahara et at., 2004). If necessary, COS-I cells were treated with 200 µg/ml cycloheximide (Sigma-Aldrich) for 2 h before images were obtained. Areas enclosed by yellow circles were photobleached at full laser power (100% laser) using the 488 nm line of an argon laser, and cells were imaged at low laser power (0.3-3.0% laser). All images were obtained as 2 µm thicknesses of one planar (xy) section. Cells were maintained at 37° C. in a temperature-controlled box. Mean fluorescence intensities were quantitated using Fluoview Tiempo time course version 4.2 software. Composite figures were prepared using Photoshop 5.0 and Illustrator 9.0 software (Adobe).

Western Blotting and Immunoprecipitation

Western blotting and immunoprecipitation were as described (Hirao et al., 1997; Mera et al., 1999; Yamaguchi et al., 2001; Kasahara et al., 2004). Cell lysates were prepared in Triton X-100 lysis buffer (50 mM HEPES, pH 7.4, 10% glycerol, 1% Triton X-100, 4 mM EDTA, 100 mM NaF, and 1 mM $Na_3VO_4$) containing protease inhibitors.

For immunoprecipitation, lysates were incubated with protein G-Sepharose beads (Amersham) precoated with anti-Src (#327) overnight at 4° C.

Subcellular Fractionation

S100 (cytosol) and P1OO (membrane) fractions were prepared as described (Yamaguchi et al., 2001). As a modification, swollen cells were homogenized with 20 strokes of a tight-fitting 1-ml Dounce homogenizer (Matsuda et al., 2006).

Results

Induction of Large Cytoplasmic Vesicles by c-Src Expression

Cells overexpressing c-Src or v-Src often exhibit large cytoplasmic vacuole-like structures (Sandilands et al., 2004; Palacios et al., 2005). To determine whether c-Src participated in formation of such structures, we generated a HeLa cell clone (Src45 cells) overexpressing c-Src in an inducible manner. When Src45 cells were treated with doxycycline (Dox), c-Src expression increased and eventually reached a steady-state level (FIG. 1A). One day after induction, Src45 cells exhibited large cytoplasmic vesicles immunopositive for c-Src (FIG. 1B). The number and size of such vesicles increased in proportion to levels of kinase-active c-Src (FIG. 1A,B; data not shown). To determine whether the kinase activity of Src-GFP (C-terminally GFP-tagged c-Src) was negatively regulated by Csk, which suppresses kinase activity of SFKs including c-Src (Nada et al., 1991; Brown and Cooper; 1996; Thomas and Brugge, 1997), we co-transfected COS-I cells with c-Src and Csk or Src-GFP and Csk. Western blots showed that the activity of Src-GFP, unlike c-Src (FIG. 1C, left), was not inhibited by Csk (FIG. 1C, right), indicating that Src-GFP is constitutively active. Indeed, FIG. 1D shows that the kinase activities of Src-GFP and oncogenic v-Src were much higher than that of c-Src due to their unresponsiveness to Csk. Next, we examined the effect of transient transfection with c-Src, Src-GFP, or v-Src (Brown and Cooper, 1996; Thomas and Brugge, 1997; Ohnishi et al., 2001) on vesicle formation in COS-1 cells. One day after transection with respective Src constructs, large cytoplasmic vesicles (>2 µm in diameter) were observed in 29.0±2.6% of cells expressing c-Src, 43.7±4.4% of cells expressing Src-GFP, and 49.0±5.4% of cells expressing v-Src (FIG. 1E). Nomarski optics indicated that every large vesicle was associated with Src-GFP (FIG. 1F). Such vesicles were not observed in parental COS-1 cells and Src45 cells not treated with Dox. These results indicate that the appearance of large vesicles requires Src kinase activity.

To confirm that c-Src kinase activity was required for induction of large vesicles, we used three catalytically inactive mutants, c-Src(K298R) (Fessart et al., 2005). Src516-GFP (lacking the C-terminal 20 amino acid residues), and v-Sre(K29SM) (Ohnishi et al., 2001). Formation of large vesicles was barely induced following transfection with these mutants (FIG. 1E), supporting the observation that c-Src catalytic activity is indispensable for large vesicle induction.

Induction of Large Vesicles by Nonpalmitoylated Lyn

Since the intracellular distribution of endogenous c-Src differs from that of endogenous Lyn in HeLa cells (Matsuda et al., 2006), we asked whether other ubiquitously expressed SFKs, such as Lyn and Fyn, functioned in large vesicle formation. Following transfection of COS-I cells with Lyn-GFP or Fyn-GFP, we observed negligible induction of large vesicles (FIG. 2A, B, D). Since Lyn and Fyn both have sites for N-myristoylation and palmitoylation, but c-Src has only an N-myristoylation site (Resh, 1994, 1999), we constructed a nonpalmitoylated Lyn-GFP mutant, Lyn(C3S)-GFP. Despite comparable levels of expression and kinase activity between Lyn-GFP and Lyn(C3S)-GFP (FIG. 2E), nonpalmitoylated Lyn strikingly Induced large vesicles in a manner similar to Src-GFP (FIG. 2C,D). These results suggest that palmitoylation inhibits large vesicle formation.

We next asked whether overexpression of SFKs led to a transformed phenotype, since induction of macropinocytosis is frequently seen in transformed cells (Swanson and Watts, 1995; Veithen et al., 1996, 1998; Amyere et al., 2000, 2002). Expression of c-Src, Src-GFP, Lyn-GFP, or Lyn(C3S)-GFP did not induce foci in C3H10T ½ fibroblasts (10T ½ cells) (FIG. 2F), but cells were easily transformed by oncogenic v-Src (FIG. 2F) (Brown and Cooper, 1996; Thomas and Brugge, 1997). These results suggest that formation of large vesicles by SFKs is not dependent on cell transformation.

c-Src-Induced Large Vesicles are Macropinosomes

Next, to ask whether c-Src-induced large vesicles functioned in solute endocytosis, COS-I cells transfected with Src-GFP were incubated in the presence of RITC-dextran (Mr 70,000). Large vesicles formed in COS-I cells were capable of taking up RITC-dextran from culture medium (FIG. 3A). Formation of large vesicles was unaffected by co-transfection with dominant-negative AP180-C (the clathrin-binding C-terminal domain of AP180; Snyers et al., 2003) (FIG. 3B), suggesting that vesicles are generated in a clathrin-independent endocytic manner. We then examined association of macropinosomal proteins with the large vesicles. Rab34 and annexin II, which are found on an early-phase subset of macropinosomes (Sun et al., 2003; Hayes et al., 2004; Sun and Endo, 2005), were associated with c-Src-anchored large vesicles at membrane ruffles (FIG. 3C,D). Some large vesicles were also associated with Rab5 (an early endosome marker: Rosenfeld et al., 2001) or Rab7 (a marker of late endosomes and lysosomes; Bucci et al., 2000) (FIG. 3E,F). Some large vesicles also expressed cathepsin D, a lysosomal protease (FIG. 3G). Large vesicles were not, however, associated with β-1,4-galactosyltransferase (GalT, a trans-Golgi resident protein) and the cation-independent MPR (a trans-Golgi network-enriched protein) (FIG. 3H,I). These results are consistent with previous reports that macropinosomes mature from early-endosome-like organelles to late-endosome-like organelles and then fuse with lysosomes without routing through the Golgi apparatus (Racoosin and Swanson, 1993; Swanson and Watts, 1995). Most large vesicles were associated with the tetraspanin CD63 (a lysosome-plasma membrane cycling protein; Kobayashi et al., 2000; Blott et al., 2001) (FIG. 3J). Moreover, formation of large vesicles in COS-I cells expressing Src-GFP was inhibited by wortmannin [an inhibitor of phosphoinositide 3-kinase (PI3-K)] (data not shown; see FIG. 8C), consistent with previous observations that PI3-K functions in macropinosome biogenesis (Araki et al., 1996; Amyere et al., 2000). Overall, these results indicate that large vesicles induced by c-Src kinase activity are bona fide macropinosomes.

Time-Lapse Monitoring of Macropinosomes with Src-GFP and GFP-CD63

Since c-Src appeared to associate with macropinosomes throughout their lifespan, we followed macropinosome formation in living cells by monitoring Src-GFP fluorescence (FIG. 1F). We observed that macropinsomes were generated at peripheral membrane ruffles and dorsal surface ruffles (FIG. 4A,B) and then migrated centripetally and occasionally fused (FIG. 4C).

Since macropinocytosis is accompanied by membrane ruffling and fusion, we assumed that macropinosomal membranes may furnish an active platform for dynamic protein trafficking. To test this hypothesis, we performed FRAP of Src-GFP on macropinosomes. COS-I cells expressing Src-GFP were pretreated with cycloheximide to block Src-GFP biosynthesis. When the area of macropinosomes was photobleached, rapid fluorescence recovery of Src-GFP on macropinosomes was observed reaching a steady-state level (FIG. 5A,D). Fluorescence recovery was inhibited by N-ethyl maleimide (NEM), which blocks numerous vesicle fusion events (Bivona et al., 2004), and partly inhibited by tannic acid, a cell-impermeable fixative known to prevent membrane fusion at the plasma membrane but not to affect intracellular membrane trafficking (Polishchuk et al., 2004) (FIG. 5B-D). Direct recruitment of Src-GFP from a cytosolic pool may contribute to fluorescence recovery, since 20-30% of Src-GFP was present in the cytosol (FIG. 5E; Alland et al., 1994). Nonetheless, based on these observations, we conclude that a large fraction of c-Src can traffic from the plasma membrane and intracellular organelles to macropinosomes through vesicle transport.

The tetraspanin CD63, which localizes to membranes but not the cytosol, was also found to associate with c-Src-anchored macropinosomes (FIGS. 3J, 6B). To examine whether CD63 was trafficked from the plasma membrane and intracellular organelles to macropinosomes with dynamics similar to those of c-Src, we co-transfected COS-1 cells with c-Src and GFP-CD63 to generate macropinosomes, because CD63 expression did not induce macropinosomes (FIG. 6A). When macropinosomal GFP-CD63 was photobleached in the presence of cycloheximide, rapid fluorescence recovery of GFP-CD63 reached a steady-state level with kinetics similar to those of Src-GFP (compare FIG. 6C-F with FIG. 5D). The rate of recovery of GFP-CD63 on peripheral macropinosomes was similar to that seen on perinuclear macropinosomes, indicating that CD63 traffics to macropinosomes from the plasma membrane and intracellular organelles such as lysosomes and late endosomes. Taken together, these results suggest that macropinosomal membranes serve as a plafform for protein trafficking throughout their migration.

Association of the c-Src N-Terminus with Macropinosomes

To find an element in c-Src responsible for association with macropinosomes, we fused the N-terminus of c-Src with GFP [Src(SH4-Unique)-GFP], a construct that preserves the N-myristoylation site but lacks the SH3, SH2 and kinase domains. We transfected COS-1 cells with Src(SH4-Unique)-GFP and assayed for macropinosome formation. Expression of Src(SH4-Unique)-GFP alone did not induce macropinocytosis (FIG. 7A,C). Co-expression of c-Src and Src(SH4-Unique)-GFP resulted in identical localization of these proteins (FIG. 7B) and expression of Src(SH4-Unique)-GFP did not block c-Src's ability to induce macropinosome formation (FIG. 7 A,B). When 10T ½ cells expressing Src(SH4-Unique)-GFP were stimulated with phorbol myristate acetate (PMA). RITC-dextran was taken up from culture medium by macropinosomes (FIG. 7C; Sun et al., 2003), and macropinosome formation at membrane ruffles and migration of vesicles toward the nucleus was monitored by Src(SH4-Unique)-GFP expression in PMA-stimulated living cells (FIG. 7D). In contrast, the analogous construct, Lyn(SH4-Unique)-GFP, was localized to membrane ruffles but not macropinosomes when IOT ½ cells expressing Lyn(SH4-Unique)-GFP were stimulated with PMA (FIG. 7E). In addition, PMA-stimulated macropinocytosis was not inhibited by treatment with SU6656, a selective Src inhibitor (FIG. 7F, see Discussion). Stimulation of HeLa cells expressing Src(SH4-Unique)-GFP with EGF induced large vesicles associated with Src(SH4-Unique)-GFP), which took up RITC-dextran from culture medium (FIG. 8A-C). These results indicate that EGF-induced macropinosomes are labeled with Src(SH4-Unique)-GFP as are PMA-induced macropinosomes. Similar results were observed in A431 cells expressing Src(SH4-Unique)-GFP (data not shown). Macropinosome formation that can be marked with Src(SH4-Unique)-GFP was blocked by wortmannin (FIG. 8C), indicating that Src(SH4-Unique)-GFP present in EGF-induced macropinosomes follows the dynamics of macropinosomes that have been described (Hewlett et al., 1994; Swanson and Watts, 1995; Araki et al., 1996; Amyere et al., 2000). Thus, the short c-Src N-terminus, which confers N-myristoylation, is critical for its association with macropinosomes.

Role of Endogenous c-Src in EGF-Induced Macropinocytosis

We examined whether activation of endogenous c-Src was involved in EGF-induced macropinocytosis. Endogenous c-Src was activated 1.9-fold 15 min after EGF stimulation of serum-starved HeLa cells. Pretreatment with SU6656 decreased c-Src activity below basal levels without affecting EGFR activation (FIG. 8D) and partly inhibited EGF-induced macropinosome formation (FIG. 8C). These results suggest that kinase activity of endogenous c-Src functions in EGF-induced macropinocytosis.

In EGF-stimulated A431 cells, newly generated macropinosomes reportedly remain in the peripheral cytoplasm where membrane ruffling occurs and return to the cell surface without fusing with organelles such as endosomes and lysosomes (Hewlett et al., 1994; Swanson and Watts, 1995).

Indeed, most macropinosomes disappeared from the cytoplasm in HeLa and A431 cells within 120 min of EGF stimulation (FIG. 8E). Since macropinosomes induced by c-Src overexpression moved centripetally and fused with lysosomes (FIGS. 3 and 4), we hypothesize that c-Src functions in trafficking of macropinosomes to lysosomes.

To test this hypothesis, we examined the effect of c-Src kinase activity on the fate of EGF-induced macropinosomes using Src45 cells, which exhibit high levels of inducible c-Src activity (FIG. 8F). To follow EGF-induced macropinosomes, Src45 cells were stimulated with EGF for 5 min in the presence of RITC-dextran. Subsequently, cells were washed, chased in medium without EGF, and assayed for localization of RITC-dextran-labeled macropinosomes to lysosomes using anti-cathepsin D (FIG. 8G,I). In the absence of Dox, co-localization of RITC-dextran with cathepsin D was minimally increased at the 60-min chase (FIG. 8G. upper parts: FIG. 8I). In contrast, co-localization of RITC-dextran with cathepsin D was strikingly enhanced in the presence of Dox (FIG. 8G, lower parts; FIG. 8I), consistent with increasing activity of c-Src (FIG. 1A). As in FIGS. 1-4, c-Src was associated with RITC-dextran-labeled macropinosomes in EGF-stimulated Src45 cells induced to overexpress c-Src (FIG. 8H). These results suggest that formation of macropinosomes that migrate to the lysosomal compartment is greatly enhanced by high fevels of c-Src kinase activity.

Discussion

In the present study, we show that via its N-terminus, c-Src associates with macropinosomes from their formation at the plasma membrane to their fusion with the lysosome. c-Src kinase activity is critically involved in macropinocytosis, but palmitoylation of SFKs plays an inhibitory role in macropinocytosis. We further show the existence of vesicle transport from the plasma membrane and intracellular organelles to macropinosomes.

Role of c-Src in Macropinosome Formation

We showed that inducible or transient c-Src expression triggers formation of large cytoplasmic vacuolar structures. Such vesicles were identified as bona fide macropinosomes due to the following characteristics (FIGS. 1 and 3): (1) their formation was accompanied by membrane ruffling (Lewis, 1931; Swanson, 1989; Swanson and Watts, 1995), (2) uptake of extracellular fluorescent dextran (Racoosin and Swanson, 1992; Hewlett et al., 1994; Sun et al., 2003; Schnatwinkel et al., 2004), (3) immunostaining with macropinosome-associated proteins (Racoosin and Swanson, 1993; Sun et al., 2003; Hayes et al., 2004), and (4) their formation is clathrin-independent (Racoosin and Swanson, 1992; Watts and Marsh, 1992).

Our findings provide evidence that a high level c-Src kinase activity, but not oncogenic transformation, is sufficient to induce rnacropinosomes (FIGS. 1 and 2), although oncogenic v-Src or K-Ras has been considered as a primary cause of macropinocytosis in transformed epithelial cells and fibroblasts (Bar-Sagi and Feramisco, 1986; Veithen et al., 1996, 1998; Amyere et al., 2000, 2002). We also showed that endogenous c-Src stimulates formation of macropinosomes. By monitoring cells with N-terminally GFP-tagged c-Src, we found that EGF-induced macropinocytosis was partly inhibited by SU6656 (a Src inhibitor) and strongly inhibited by wortmannin (a PI3-K inhibitor) (FIG. 8C). Previous reports showed that PI3-K activity is essential for macropinocytosis, and that oncogenic v-Src induces macropinocytosis through activation of PI3-K (Araki et al., 1996; Amyere et al., 2000, 2002). Thus, we propose that c-Src kinase activity participates in signaling to activate P13-K, which is essential for EGF-induced macropinosome formation. However, the finding that SU6656 treatment did not inhibit PMA-induced macropinosome formation (FIG. 7F) suggests that an effector of PMA such as protein kinase C may be positioned downstream of c-Src or PMA signaling for macropinocytosis may not involve c-Src activation.

Role of c-Src in Macropinosome Trafficking

Since c.-Src activity increased the number of macropinosomes in the lysosomal compartment following EGF stimulation (FIG. 8), we hypothesize that c-Src activity functions in trafficking of macropinosomes to lysosomes and/or the fusion of macropinosomes to lysosomes. This finding could explain why c-Src is abundantly expressed in cell types exhibiting high pinocytic activity, such as osteoclasts and macrophages. Emerging evidence supports the conclusion that c-Src functions in macropinosomal maturation as well as formation, although how c-Src-regulated trafficking of macropinosomes occurs is unknown. For example, several SFK substrates and/or binding proteins, such as annexin II and PI3-K, are associated with macropinosomes and phagosomes (Amyere et al., 2002). Different sets of proteins are phosphorylated and dephosphorylated at precise intervals during phagosomal maturation (Emans et at., 1996). In addition, the major macropinosomal components Rab5 and Rab7 are activated by v-Src through an unknown mechanism (Palacios et al., 2005). Membrane-cytoskeleton interactions underlying organelle positioning and motility are regulated by Rho-Dia-Src signaling cascades (Gasman et al., 2003), which might be applicable to macropinosome trafficking through an actin-mediated process.

Continuous Association of c-Src with Macropinosomes

Although macropinosomes and other endocytic vesicles can be visualized following uptake of extracellular solutes such as RITC-dextran (FIG. 3A), little progress has been made in determining mechanisms that regulate the generation and migration of macropinosomes because there are no specific markers available. We showed that c-Src is associated with macropinosomes at all stages of their development (FIGS. 1-4). A short c-Src N-terminal sequence lacking major protein-interacting domains is sufficient for continuous association with macropinosomes, and GFP-tagged sequence enabled us to examine the dynamics of macropinocytosis induced by PMA or EGF in living cells (FIGS. 7 and 8).

It has been hypothesized that macropinosomes may acquire lysosomal membrane proteins before fusion with lysosomes is complete and recycle them to the plasma membrane by the shuttling of small vesicles (Swanson, 1989; Raccosin and Swanson, 1993; Swanson and Watts, 1995). However, evidence for such a mechanism awaits development of suitable markers for macropinosomes. In this study, by FRAP of Src-GFP- or GFP-CD63-associated macropinosomes, the fluorescence recovery of Src-GFP on macropinosomes was inhibited by NEM and partly by tannic acid (FIG. 5B-D). Although a fraction of c-Src was present in the cytosol (FIG. 5E, Alland et al., 1994), the kinetics of fluorescence recovery of Src-GFP (FIG. 5) was similar to that of GFP-CD63, which spans the phospholipid bilayer four times (FIG. 6). Thus, we provide evidence for the existence of vesicle transport from the plasma membrane and intracellular organelles to macropinosomes.

Role of Palmitoylation of SFKs in Induction of Macropinocytosis c-Src, a nonpalmitoylated SFK, induces constitutive macropinocytosjs in a kinase activity dependent manner and is associated with macropinosomes during the entire process of macropinocytosis (FIGS. 1, 3-5). However, Lyn and Fyn, both of which are palmitoylated, do not appreciably induce macropinocytosis. Intriguingly, nonpalmitoylated Lyn(C3S)-GFP can induce macropinocytosis (FIG. 2). Thus, the c-Src N-terminus, which confers N-myristoylation but not palmitoylation, plays an important role in induction of macropinocytosis and association with macropinosomes (compare FIG. 7D with E). Furthermore, the Arf-6 GTPase, which has an N-myristoylation site but not a palmitoylation site, is also associated with macropinosomes and involved in macropinocytosis (Resh, 1999; Brown et al., 2001), suggesting the N-myristoylated region may be generally important for macropinocytosis.

Recent findings indicate that inhibition of Fcγ receptor-mediated phagocytosis in macrophages by Csk overexpression is rescued by expression of kinase-active Lyn and kinase-active p59$^{Hck}$, a palmitoylated isoform of Hck, but not by expression of kinase-active c-Src (Suzuki et al., 2000). It is interesting that phagocytosis but not macropinocytosis is regulated by palmitoylated SFKs. Palmitoylation is thought to regulate SFK signaling pathways by modulating their intracellular localization (Resh, 1999; Bijlmakers and Marsh, 2003). It has been suggested that Fcγ receptor-mediated phagocytosis is stimulated by palmitoylated SFKs, which are associated with detergent-resistant membranes (DRM), but not by c-Src, which is excluded from DRM (Suzuki et al., 2000), since tyrosine phosphorylation of the Fcγ receptor and the subsequent signaling controlled by SFKs occur primarily at DRM and accessibility of SFKs to DRM requires palmitoylation (Resh, 1999; Honda et al., 2000; Bijimakers and Marsh, 2003; Kwiatkowska et al., 2003).

Recently, we reported that Lyn is biosynthetically transported to the plasma membrane via the Golgi apparatus along the secretory pathway (Kasahara et al., 2004). Lck, a palmitoylated SFK, was also reported to follow the secretory pathway (Bijlmakers and Marsh, 1999, 2003). In contrast to Lyn and Lck, c-Src and p61$^{Hck}$, which are nonpalmitoylated, are localized to late endosomes and lysosomes and are transported to the plasma membrane from these organelles (Sandilands et al., 2004; Cougoule et al., 2005; our unpublished data). Moreover, p61$^{Hck}$, but not p59$^{Hck}$, triggers the biogenesis of podosomes, actin-rich rings at the ventral cell surface, by exocytosis from lysosomes (Cougcule et al., 2005). These results suggest that nonpalmitoylated SFKs, such as c-Src and p61$^{Hck}$, may function in biogenesis of lysosome-related membrane vesicles such as macropinosomes and podosomes.

CONCLUSION

This work shows that SFKs function in macropinocytosis in a kinase- and acylation state-dependent manner. Rapid transport of macropinosomes is dynamic and can be analyzed by time-lapse monitoring and FRAP of Src-GFP. It is now of interest to dissect the dynamics of macropinosomes in living phagocytic cells as well as in growth factor-stimulated cells using Src(SH4-Unique)-GFP.

Various publications are cited herein. The following references are incorporated in their entirety by reference herein.

Alland L, Peseckis S M, Atherton R E, Berthiaume L., Resh M D., 1994. Dual myristylation and palmitylation of Src family member p58$^{fyn}$ affects subcellular localization. J Biol Chem, 269:16701-16706.

Amyere M, Payrastre B, Krause U, van Der Smissen P, Veithen A, Courtoy P J, 2000. Constitutive macropinocytosis in oncogene-transformed fibroblasts depends on sequential permanent activation of phosphoinositide 3-kinase and phospholipase. C. Mol Biol Cell, 11:3453-3467.

Amyere M, Mettlen M, van DerSmissen P, Platek A, Payrastre B, Veithen A, Courtoy P J, 2002. Origin, originality, functions, subversions and molecular signaling of macropinocytosis, Int. J. Med. Microbiol., 29 1:487-494.

Araki N. Johnson M T, Swanson J A, 1996. A role for phosphoinostitide 3-kinases in the completion of macropinocytosis and phagocytosis by macrophages. J Cell Biol 135: 1249-1260.

Bar-Sagi D, Feramisco J R, 1996. Induction of membrane ruffling and fluid-phase pinocytosis in quiescent fibroblasts by ras proteins. Science 233:1061-1068.

Bard F, Mazelin L, Péchhoux-Longin C, Malhotra V, Jurdic P., 2003. Src regulates Golgi structure and KDEL receptor-dependent retrograde transport to the endoplasmic reticulum. J Biol Chem 278:46601-6606.

Bijlmakers M J E, Marsh M, 1999. Trafficking of an acylated cytosolic protein: Newly synthesized p56$^{lck}$ travels to the plasma membrane via the exocytic pathway. J Cell Biol 145:457-468.

Bijlmakers M J E, Marsh M. 2003. The on-off story of protein palmitoylation. Trends Cell Biol 13:32-42.

Bivona T G, Wiener H H, Ahearn I M, Silletti J, Chiu V K, Philips M R, 2004. Rap 1 up-regulation and activation on plasma membrane regulates T cell adhesion. J Cell Biol 164:461-470.

Bjorge J D, Bellagamba C, Cheng H C, Tanaka A, Wang J H, Fujita D J, 1995. Characterization of two activated mutants of human pp60$^{c-src}$ that escape c-Src kinase regulation by distinct mechanisms. J Biol Chem 270:24222.-24228.

Blake R A, Broome M A, Liu X, Wu J, Gishizky M, Sun L, Courtneidge S A, 2000. SU6656, a selective Src family kinase inhibitor, used to probe growth factor signaling. Mol Cell Biol 20:9018-9027.

Blott E J, Bossi G, Clark R, Zvelebil M, Griffiths G M, 2001. Fas ligand is targeted to secretory lysosomes via a proline-rich domain in its cytoplasmic tail. J Cell Sci 114:2405-2416.

Brown M T, Cooper J A, 1996. Regulation, substrates and functions of src. Biochim Biophys Acta 1287:121-149.

Brown F D, Rozelle A L, Yin H L, Balla T, Donaldson J G. 2001. Phosphatidylinositol 4,5-bisphosphate and Arf6-regulated membrane traffic. J Cell Biol 154: 1007-1017.

Bucci C, Thomsen P, Nicoziani P, McCarthy J, van Deurs B, 2000. Rab7: A key to lysosome biogenesis. Mol Biol Cell 11:467-480.

Cardelli J, 2001. Phagocytosis and macropinocytosis in dictyostelium: Phosphoinositide-based processes, biochemically distinct. Traffic 2:311-320.

Conner S D, Schmid S L, 2003. Regulated portals of entry into the cell. Nature 422:37-44.

Cougoule C, Carreno S, Castandet J, Labrousse A, Astarie-Dequeker C, Poincloux R, Cavec V L, Maridonneau-Parini I, 2005. Activation of the lysosome-associated p61$^{Hck}$ isoform triggers the biogenesis of podosomes. Traffic 6:682-694.

Ellerbroek S M, Werrerberg K, Arthur W T, Dunty J M, Bowman D R, DeMali K A, Der C. Burridge K, 2004. SGEF, a RhoG guanine nucleotide exchange factor that stimulates macropinocytosis. Mol Biol Cell 15:3309-3319.

Emans N, Nzala N N, Desjardins M, 1996. Protein phosphorylation during phagosome maturation. FEBS Lett 398:37-42.

Fessart X, Simaan M, Laporte S A, 2005. c-Src regulates clathrin adapter protein 2 interaction between with beta-arrestin and the angiotensin II type I receptor during clathrin-mediated internalization. Mol Endocrinol 19:491-503.

Gasman S, Kalaidzidis Y, Zerial M, 2003. RhoD regulates endosome dynamics through Diaphanous-related formin and Src tyrosine kinase. Nat Cell Biol 5: 195-204.

Hayes M J, Merrifield C J, Shao D, Ayala-Sannartin J, Schorey C D, Levine T P, Proust J, Curran J, Bailly M, Moss S E, 2004. Annexin 2 binding to phosphatidylinositol 4,5-biphosphate on endocytic vesicles is regulated by the stress response pathway. J Biol Chem 279:14157-14164.

Hewlett L J, Prescott A R, Watts C, 1994. The coated pit and macropinocytic pathways serve distinct endosome populations, J Cell Biol 124:689-703.

Hirao A, Hamaguchi I, Suda T, Yamaguchi N, 1997. Translocation of the Csk homologous kinase (Chk/Hyl) controls activity of CD36-associated Lyn tyrosine kinase in thrombinstimulated platelets. EMBO J 16:2342-2351.

Honda Z, Suzuki T, Kono H, Okada M, Yarnamoto T, Ra C, Morita Y, Yamamoto K. 2000. Sequential requirements of the N-terminal palmitoylation site and SH2 domain of Src family kinases in the initiation and progression of F$_{ca}$RI signaling. Mol Cell Biol 20:1759-1771.

Kasahara K, Nakayama Y, Ikeda K, Fukushima Y, Matsuda D, Horimoto S, Yamaguchi N, 2004. Trafficking of Lyn through the Golgi caveolin involves the charged residues on αE and α helices in the kinase domain. J Cell Biol 165:641-652.

Kobayashi T, Vischer U M, Rosnoblet C, Lebrand C, Lindsay M, Parton R G, Kruithof E K O, Gruenberg J, 2000. The tetraspanin CD63/lamp3 cycles between endocytic and secretory compartments in human endothelial cells. Mol Biol Cell J 1:1829-1843.

Kwiatkowska K, Frey J, Sobota A, 2003. Phosphorylation of FcγRIIA is required for the receptor-induced actin rearrangement and capping: The role of membrane rafts. J Cell Sci 115:537-550.

Lewis W H, 1931. Pinocytosis. Johns Hopkins Hosp Bull 49: 17-27.

Lowell C A, Niwa M, Soriano P, Varmus H E, 1996. Deficiency of the Hck and Src tyrosine kinases results in extreme levels of extramedullay hematopoiesis. Blood 87: 1780-1792.

Matsuda D, Nakayama Y, Horimoto S, Kuga T, Ikeda K, Kasahara K, Yamaguchi N, 2006. Involvement of Golgi-associated Lyn tyrosine kinase in the translocation of annexin 11 to the endoplasmic reticulum under oxidative stress. Exp Cell Res 312:1205-1217.

Mera A, Suga M, Ando M, Suda T, Yamaguchi N, 1999. Induction of cell shape changes through activation of the interleukin-3 common β chain receptor by the RON receptor tyrosine kinase. J Biol Chem 274:15766-15174.

Miyazaki J, Takaki S, Araki K, Tashiro F, Tominaga A, Takatsu K. Yamamura K. 1989. Expression vector system based on the chicken β-actin promoter directs efficient production of interleukin-5. Gene 79:269-277.

Nada S, Okada M, McAuley A, Cooper J A, Nakagawa H, 1991. Cloning of a complementary DNA for a protein-tyrosine kinase that specifically phosphorylates a negative regulatory of p60$^{c-src}$. Nature 351:69-71.

Nakayama Y, Yamaguchi N, 2005. Multi-lobulation of the nucleus in prolonged S phase by nuclear expression of Chk tyrosine kinase. Exp Cell Res 304:570-581.

Nakayama Y, Kawana A, Igarashi A, Yamaguchi N, 2006. Involvement of the N-terminal unique domain of Chk tyrosine kinase in Chk-induced tyrosine phosphorylation in the nucleus. Exp Cell Res 312:2252-2263.

Ohnishi H, Yamamori S, Ono K, Aoyagi K, Kondo S, Takahashi M. 2001. A src family tyrosine kinase inhibits neurotransmitter release from neuronal cells. Proc Natl Acad Sci USA 98: 10930-10935.

Palacios F, Tushir J S, Fujita Y, D'Souza-Schorey C, 2005. Lysosomal targeting of E-cadherin: A unique mechanism for the down-regulation of cell-cell adhesion during epithelial to mesenchymal transitions. Mol Cell Biol 25:389-402.

Polishchuk R, Pentima A D, Lippincott-Schwartz J, 2004. Delivery of raft-associated, GPI-anchored proteins to the apical surface of polarized MDCK cells by a transcytotic pathway. Nat Cell Biol 6:297-307.

Racoosin E L, Swanson J A, 1992. M-CSF induced macropinocytosis increases solute endocytosis but not receptor-mediated endocytosis in mouse macrophages. J Cell Sci 102:867-880.

Racoosin E L, Swanson J A, 1993. Macropinosome maturation and fusion with tubular lysosomes in macrophages, J Cell Biol 121:1011-1020.

Resh M D, 1994. Myristylation and palmitylation of Src family members: The fats of matter. Cell 76:411-413.

Rash M D, 1999. Fatty acylation of proteins: New insights into membrane targeting of myristoylated and palmitoylated proteins. Biochim Biophys Acta 145 I: 1-16.

Rosenfeld J L, Moore R H, Zimmer K-P, Alpizar-Foster E, Dai W, Zarka M N, Knoll B J, 2001. Lysosome proteins are redistributed during expression of a GTP-hydrolysis-defective rab5a. J Cell Sci 114:4499-4508.

Sandilands E, Cans C, Fincham V J, Brunton V G, Mellor H, Prendergast G C, Norman J C, Superti-Furga G, Frame M C, 2004. RhoB and actin polymerization coordinate Src activation with endosome-mediated delivery to the membrane. Dev Cell 7:855-869.

Schnatwinkel C, Christoforidis S, Lindsay M R, Uttenwiler-Joseph S, Wilm M, Parton R G, Zerial M, 2004. The Rab5 effector Rabankyrin-5 regulates and coordinates different endocytic mechanisms. PLoS Biol 2:1363-1380.

Snyers L, Zwicki H, Blaas D, 2003. Human rhinovirus type 2 is internalized by clathrin-mediated endocytosis. J Virol 77:5360-5369.

Stein P L, Vogel H, Soriano P, 1994. Combined deficiencies of Src, Fyn, and Yes tyrosine kinases in mutant mice. Genes Dev 8:1999-2007.

Sun P, Endo T, 2005. Assays for functional properties of Rab34 in macropinosome formation. Methods Enzymol 403:229-243.

Sun P, Yamamoto H, Suetsugu S, Miki H, Takenawa T, Endo T, 2003. Small GTPase Rah/Rab34 is associated with membrane ruffles and macropinosomes and promotes macropinosome formation. J Biol Chem 278:4063-4071.

Suzuki T, Kono H, Hirose N, Okada M, Yamamoto T, Yamamoto K, Honda Z, 2000. Differential involvement of Src family kinasas in Fcγ receptor-mediated phagocytosis. J Immunol 165:473-482.

Swanson J A, 1989. Phorbol esters stimulate macropinocytosis and solute flow through macrophages. J Cell Sci 94:135-142.

Swanson J A, Watts C, 1995. Macropinocytosis. Trends Cell Biol 5:424-428.

Tada J, Omine M, Suda T, Yamaguchi N, 1999. A common signaling pathways via Syk and Lyn tyrosine kinases generated from capping of the sialomucins CD34 and CD43 in immature hematopoietic cells. Blood 93:3723-3735.

Tezuka T, Umemori H, Akiyama T, Nakanishi S, Yamamoto T, 1999. PSD-95 promotes Fyn-mediated tyrosine phosphorylation of the N-metyl-D-aspartate receptor subunit NR2A. Proc Natl Acad Sci USA 96:435-440.

Thomas S M, Brugge J S, 1997. Cellular functions regulated by Src family kinases. Annu Rev Cell Dev Biol 13:513-609.

Thomas S M, Soriano P, Imamoto A, 1995. Specific and redundant roles of Src and Fyn in organizing the cytoskeleton. Nature 376:267-271.

Umeda A, Fujita H, Kuronita T, Hirosako K, Himeno M, Tanaka Y, 2003. Distribution and trafficking of MPR300 is normal in cells with cholesterol accumulated in late endocytic compartments: Evidence for early endosome-to-TGN trafficking of MPR300. J Lipid Res 44: 1821-1832.

Veithen A, Cupers P, Baudhuin P, Courtoy P J, 1996. v-Src induced constitutive macropinocytosis in rat fibroblasts. J Cell Sci 109:2005-2012.

Veithen A, Amyere M, Smissen P V D, Cupers P, Courtoy P J, 1998. Regulation of macropinocytosis in v-Src-transformed fibroblasts: Cyclic AMP selectively promotes regulation of macropinosomes. J Cell Sci 111:2329-2335.

Ware M F, Tice D A, Parsons S J, Lauffenburger D A, 1997. Overexpression of cellular Src in fibroblasts enhances endocytic internalization of epidermal growth factor receptor. J Biol Chem 28:30185-30190.

Watts C, Marsh M, 1992. Endocytosis: What goes in and how? J Cell Sci 103:1-8.

Yamaguchi N, Fukuda M N, 1995. Golgi retention mechanism of β-1,4-galactosyltransferase: Membrane-spanning domain-dependent homodimerization and association with α- and β-tubulins. J Biol Chem 270:12170-12176, Yamaguchi N, Nakayama Y, Urakami T, Suzuki S, Nakamura T, Suda T, Oku N, 2001. Overexpression of the Csk homologous kinase (Chk tyrosine kinase) induces multinucleation: A possible role for chromosome-associated Chk in chromosome dynamics. J Cell Sci 114:1631-1641.

Yamanashi Y, Fukushige S, Semba K, Sukegawa J, Miyajima N, Matsubara K, Yamamoto T, Toyoshima K, 1987. The yes-related cellular gene lyn encodes a possible tyrosine kinase similar to p56$^{lck}$. Mol Cell Biol 7:237-243.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

I claim:

1. A mammalian cell line transformed with a plasmid comprising SEQ ID NO: 1, the mammalian cell line overexpressing inducible c-Src.

2. A human cell line transformed with a plasmid comprising SEQ ID NO: 1, the human cell line overexpressing c-Src in an inducible manner.

3. A HeLa cell clone line transformed with a plasmid comprising SEQ ID NO: 1, the HeLa cell clone line overexpressing c-Src in an inducible manner.

4. A Src45 cell line transformed with a plasmid comprising SEQ ID NO: 1.

* * * * *

SEQUENCE LISTING

<160> NUMBER OF SEQ ID NOS: 7

<210> SEQ ID NO 1
<211> LENGTH: 6676
<212> TYPE: DNA
<213> ORGANISM: Artificial
<220> FEATURE:
<223> OTHER INFORMATION: Plasmid

<400> SEQUENCE: 1

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
```

```
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggaacc    720
aaaatcaacg ggactttcca aaatgtcgta acaactccgc cccattgacg caaatgggcg    780
gtaggcgtgt acggtgggag gtctatataa gcagagctct ccctatcagt gatagagatc    840
tccctatcag tgatagagat cgtcgacgag ctcgtttagt gaaccgtcag atcgcctgga    900
gacgccatcc acgctgtttt gacctccata agagacaccg ggaccgatcc agcctccgga    960
ctctagcgtt taaacttaag cttggtaccg agctcggatc cactagtcca gtgtggtgga   1020
attccgacca ccatgggtag caacaagagc aagcccaagg atgccagcca gcggcgccgc   1080
agcctggagc ccgccgagaa cgtgcacggc gctggcgggg gcgctttccc cgcctcgcag   1140
acccccagca agccagcctc ggccgacggc accgcggcc ccagcgcggc cttcgccccc   1200
gcggccgccg agcccaagct gttcggaggc ttcaactcct cggacaccgt cacctccccg   1260
cagagggcgg gcccgctggc cggtggagtg accacctttg tggccctcta tgactatgag   1320
tctaggacgg agacagacct gtccttcaag aaaggcgagc ggctccagat tgtcaacaac   1380
acggagggag actggtggct ggcccactcg ctcagcacag gacagacagg ctacatcccc   1440
agcaactacg tggcgccctc cgactccatc caggctgagg agtggtattt tggcaagatc   1500
accagacggg agtcagagcg gttactgctc aatgcagaga acccgagagg gaccttcctc   1560
gtgcgagaaa gtgagaccac gaaaggtgcc tactgcctct cagtgtctga cttcgacaac   1620
gccaagggcc tcaacgtgaa gcactacaag atccgcaagc tggacagcgg cggcttctac   1680
atcacctccc gcacccagtt caacagcctg cagcagctgg tggcctacta ctccgaacac   1740
gccgatggcc tgtgccaccg cctcaccacc gtgtgcccca gtccaagcc gcagactcag   1800
ggcctggcca aggatgcctg ggagatccct cgggagtcgc tgcggctgga ggtcaagctg   1860
ggccagggct gctttggcga ggtgtggatg gggacctgga acggtaccac cagggtggcc   1920
atcaaaaccc tgaagcctgg cacgatgtct ccagaggcct cctgcaggga ggcccaggtc   1980
atgaagaagc tgaggcatga aagctggtg cagttgtatg ctgtggtttc agaggagccc   2040
atttacatcg tcacggagta catgagcaag gggagtttgc tggactttct caaggggag   2100
acaggcaagt acctgcggct gcctcagctg gtggacatgg ctgctcagat cgcctcaggc   2160
atggcgtacg tggagcggat gaactacgtc accggac cttcgtgcagc caacatcctg   2220
gtgggagaga acctggtgtg caaagtggcc gactttggc tggctcggct cattgaagac   2280
aatgagtaca cggcgcggca aggtgccaaa ttccccatca gtggacggc tccagaagct   2340
gccctctatg gccgcttcac catcaagtcg gacgtgtggt ccttcgggat cctgctgact   2400
gagctcacca caaagggacg ggtgcccta cctgggatgg tgaaccgcga ggtgctggac   2460
caggtggagc ggggctaccg gatgcccgc ccgccggagt gtcccgagtc cctgcacgac   2520
```

```
ctcatgtgcc agtgctggcg gaaggagcct gaggagcggc ccaccttcga gtacctgcag      2580
gccttcctgg aggactactt cacgtccacc gagcccagt accagcccgg ggagaacctc       2640
taggcacagc tcgagtctag agggcccgtt taaacccgct gatcagcctc gactgtgcct      2700
tctagttgcc agccatctgt tgtttgcccc tcccccgtgc cttccttgac cctggaaggt      2760
gccactccca ctgtcctttc ctaataaaat gaggaaattg catcgcattg tctgagtagg      2820
tgtcattcta ttctgggggg tggggtgggg caggacagca aggggagga ttgggaagac       2880 aatagcaggc atgctgggga tgcggtgggc tctatggctt ctgaggcgga agaaccagc       2940 tggggctcta gggggtatcc ccacgcgccc tgtagcggcg cattaagcgc ggcgggtgtg      3000
gtggttacgc gcagcgtgac cgctacactt gccagcgccc tagcgcccgc tcctttcgct     3060
ttcttccctt cctttctcgc cacgttcgcc ggctttcccc gtcaagctct aaatcggggg     3120 ctcccttag ggttccgatt tagtgcttta cggcacctcg accccaaaaa acttgattag       3180
ggtgatggtt cacgtagtgg gccatcgccc tgatagacgg ttttcgccc tttgacgttg      3240 gagtccacgt tctttaatag tggactcttg ttccaaactg gaacaacact caaccctatc     3300
tcggtctatt cttttgattt ataagggatt ttgccgattt cggcctattg gttaaaaaat     3360
gagctgattt aacaaaaatt taacgcgaat taattctgtg gaatgtgtgt cagttagggt     3420
gtggaaagtc cccaggctcc ccagcaggca gaagtatgca aagcatgcat ctcaattagt     3480
cagcaaccag gtgtggaaag tccccaggct ccccagcagg cagaagtatg caaagcatgc     3540
atctcaatta gtcagcaacc atagtcccgc ccctaactcc gcccatcccg ccctaactc      3600 cgcccagttc cgcccattct ccgccccatg gctgactaat ttttttatt tatgcagagg      3660 ccgaggccgc ctctgcctct gagctattcc agaagtagtg aggaggcttt tttggaggcc     3720
taggcttttg caaaaagctc ccgggagctt gtatatccat tttcggatct gatcagcacg     3780
tgttgacaat taatcatcgg catagtatat cggcatagta taatacgaca aggtgaggaa     3840
ctaaaccatg gccaagttga ccagtgccgt tccggtgctc accgcgcgcg acgtcgccgg     3900
agcggtcgag ttctggaccg accggctcgg gttctcccgg gacttcgtgg aggacgactt     3960
cgccggtgtg gtccgggacg acgtgaccct gttcatcagc gcggtccagg accaggtggt     4020
gccggacaac accctggcct gggtgtgggt gcgcggcctg gacgagctgt acgccgagtg     4080
gtcggaggtc gtgtccacga acttccggga cgcctccggg ccggccatga ccagatcgg      4140 cgagcagccg tgggggcggg agttcgccct gcgcgacccg gccggcaact gcgtgcactt     4200
cgtggccgag gagcaggact gacacgtgct acgagatttc gattccaccg ccgccttcta     4260
tgaaaggttg gcttcggaa tcgttttccg ggacgccggc tggatgatcc tccagcgcgg      4320
ggatctcatg ctggagttct tcgcccaccc caacttgttt attgcagctt ataatggtta     4380
caaataaagc aatagcatca caaatttcac aaataaagca ttttttcac tgcattctag      4440 ttgtggtttg tccaaactca tcaatgtatc ttatcatgtc tgtataccgt cgacctctag     4500
ctagagcttg gcgtaatcat ggtcatagct gtttcctgtg tgaaattgtt atccgctcac     4560
aattccacac aacatacgag ccggaagcat aaagtgtaaa gcctggggtg cctaatgagt     4620
gagctaactc acattaattg cgttgcgctc actgcccgct ttccagtcgg gaaacctgtc     4680
gtgccagctg cattaatgaa tcggccaacg cgcggggaga ggcggtttgc gtattgggcg     4740
ctcttccgct tcctcgctca ctgactcgct gcgctcggtc gttcggctgc ggcgagcggt     4800
atcagctcac tcaaaggcgg taatacggtt atccacagaa tcaggggata acgcaggaaa     4860
gaacatgtga gcaaaaggcc agcaaaaggc caggaaccgt aaaaaggccg cgttgctggc     4920
```

-continued

```
gtttttccat aggctccgcc ccectgacga gcatcacaaa aatcgacgct caagtcagag    4980
gtggcgaaac ccgacaggac tataaagata ccaggcgttt ccccctggaa gctccctcgt    5040
gcgctctcct gttccgaccc tgccgcttac cggatacctg tccgcctttc tcccttcggg    5100
aagcgtggcg ctttctcata gctcacgctg taggtatctc agttcggtgt aggtcgttcg    5160
ctccaagctg ggctgtgtgc acgaaccccc cgttcagccc gaccgctgcg ccttatccgg    5220
taactatcgt cttgagtcca acccggtaag acacgactta tcgccactgg cagcagccac    5280
tggtaacagg attagcagag cgaggtatgt aggcggtgct acagagttct tgaagtggtg    5340
gcctaactac ggctacacta agaacagt atttggtatc tgcgctctgc tgaagccagt     5400
taccttcgga aaaagagttg gtagctcttg atccggcaaa caaaccaccg ctggtagcgg    5460
tttttttgtt tgcaagcagc agattacgcg cagaaaaaaa ggatctcaag aagatccttt    5520
gatcttttct acggggtctg acgctcagtg aacgaaaac tcacgttaag ggattttggt     5580
catgagatta tcaaaaagga tcttcaccta gatcctttta aattaaaaat gaagttttaa    5640
atcaatctaa agtatatatg agtaaacttg gtctgacagt taccaatgct taatcagtga    5700
ggcacctatc tcagcgatct gtctatttcg ttcatccata gttgcctgac tccccgtcgt    5760
gtagataact acgatacggg agggcttacc atctggcccc agtgctgcaa tgataccgcg    5820
agacccacgc tcaccggctc cagatttatc agcaataaac cagccagccg aagggccga    5880
gcgcagaagt ggtcctgcaa ctttatccgc ctccatccag tctattaatt gttgccggga    5940
agctagagta gtagttcgc cagttaatag tttgcgcaac gttgttgcca ttgctacagg    6000
catcgtggtg tcacgctcgt cgtttggtat ggcttcattc agctccggtt cccaacgatc    6060
aaggcgagtt acatgatccc ccatgttgtg caaaaaagcg gttagctcct tcggtcctcc    6120
gatcgttgtc agaagtaagt tggccgcagt gttatcactc atggttatgg cagcactgca    6180
taattctctt actgtcatgc catccgtaag atgcttttct gtgactggtg agtactcaac    6240
caagtcattc tgagaatagt gtatgcggcg accgagttgc tcttgcccgg cgtcaatacg    6300
ggataatacc gcgccacata gcagaacttt aaaagtgctc atcattggaa aacgttcttc    6360
ggggcgaaaa ctctcaagga tcttaccgct gttgagatcc agttcgatgt aacccactcg    6420
tgcacccaac tgatcttcag catcttttac tttcaccagc gtttctgggt gagcaaaaac    6480
aggaaggcaa aatgccgcaa aaaagggaat aagggcgaca cggaaatgtt gaatactcat    6540
actcttcctt tttcaatatt attgaagcat ttatcagggt tattgtctca tgagcggata    6600
catatttgaa tgtatttaga aaaataaaca ataggggtt ccgcgcacat ttccccgaaa     6660
agtgccacct gacgtc                                                   6676
```

<210> SEQ ID NO 2
<211> LENGTH: 25
<212> TYPE: DNA
<213> ORGANISM: Artificial
<220> FEATURE:
<223> OTHER INFORMATION: Primer

<400> SEQUENCE: 2
aaagaattcc gaccatgggt agcaa                                          25

<210> SEQ ID NO 3
<211> LENGTH: 29
<212> TYPE: DNA
<213> ORGANISM: Artificial
<220> FEATURE:
<223> OTHER INFORMATION: Primer

```
<400> SEQUENCE: 3
tttctcgagc tgtgcctaga ggttctccc                                    29

<210> SEQ ID NO 4
<211> LENGTH: 41
<212> TYPE: DNA
<213> ORGANISM: Artificial
<220> FEATURE:
<223> OTHER INFORMATION: Primer

<400> SEQUENCE: 4
caccgcgagc gggaaatatg ggatcgataa aatcaaaagg g                      41

<210> SEQ ID NO 5
<211> LENGTH: 41
<212> TYPE: DNA
<213> ORGANISM: Artificial
<220> FEATURE:
<223> OTHER INFORMATION: Primer

<400> SEQUENCE: 5 ccctttttgat tttatcgatc ccatatttcc cgctcgcggt g                     41

<210> SEQ ID NO 6
<211> LENGTH: 31
<212> TYPE: DNA
<213> ORGANISM: Artificial
<220> FEATURE:
<223> OTHER INFORMATION: Primer

<400> SEQUENCE: 6
aaacacgcgt cgagcgggaa atatgggatg t                                 31

<210> SEQ ID NO 7
<211> LENGTH: 34
<212> TYPE: DNA
<213> ORGANISM: Artificial
<220> FEATURE:
<223> OTHER INFORMATION: Primer

<400> SEQUENCE: 7
ccaaagtttg atttctaggt ctccaccggt aaga                              34
```